US008731659B2

(12) United States Patent
Hansen et al.

(10) Patent No.: US 8,731,659 B2
(45) Date of Patent: May 20, 2014

(54) MULTI-SITE LEAD/SYSTEM USING A MULTI-POLE CONNECTION AND METHODS THEREFOR

(75) Inventors: David J. Hansen, Oakdale, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1011 days.

(21) Appl. No.: 11/230,989

(22) Filed: Sep. 20, 2005

(65) Prior Publication Data

US 2007/0066998 A1 Mar. 22, 2007

(51) Int. Cl.
A61N 1/362 (2006.01)

(52) U.S. Cl.
USPC .............................................. 607/9

(58) Field of Classification Search
USPC ...................................... 607/9–11
See application file for complete search history.

(56) References Cited

U.S. PATENT DOCUMENTS

| | | | |
|---|---|---|---|
| 6,128,535 A | 10/2000 | Maarse | |
| 6,253,106 B1 | 6/2001 | Legay et al. | |
| 6,295,475 B1 | 9/2001 | Morgan | |
| 6,327,498 B1 | 12/2001 | Kroll | |
| 6,473,645 B1 | 10/2002 | Levine | |
| 6,477,417 B1 | 11/2002 | Levine | |
| 6,584,362 B1 | 6/2003 | Scheiner et al. | |
| 6,606,516 B2 | 8/2003 | Levine | |
| 6,615,089 B1 | 9/2003 | Russie et al. | |
| 6,643,546 B2 * | 11/2003 | Mathis et al. | 607/9 |
| 6,643,550 B2 | 11/2003 | Westlund et al. | |
| 6,662,055 B1 | 12/2003 | Prutchi | |
| 6,728,575 B2 | 4/2004 | Hedberg | |
| 2003/0078623 A1* | 4/2003 | Weinberg et al. | 607/9 |
| 2003/0153953 A1* | 8/2003 | Park et al. | 607/17 |
| 2003/0204232 A1 | 10/2003 | Sommer et al. | |
| 2006/0041280 A1 | 2/2006 | Stahmann et al. | |

FOREIGN PATENT DOCUMENTS

| | | |
|---|---|---|
| EP | 1184050 A2 | 3/2002 |
| EP | 1529551 A1 | 5/2005 |
| WO | WO-02064205 A2 | 8/2002 |

OTHER PUBLICATIONS

"International Search Report and Written Opinion for Application No. PCT/US2006/036334, Mailed Jan. 30, 2007", 13 Pages.
"European Application Serial No, 06803801.7, Response filed Sep. 14, 2011 to European Examination mailed May 13, 2011", 7 pgs.
"European Application Serial No. 06803801.7, Examination Notification mailed May 13, 2011", 3 pgs.
"European Application Serial No. 06803801.7, Examination Notification Art. 94(3) mailed Aug. 7, 2013", 4 pgs.

* cited by examiner

Primary Examiner — Rex R Holmes
(74) Attorney, Agent, or Firm — Schwegman, Lundberg & Woessner, P.A.

(57) ABSTRACT

One or more multi-electrode lead coupled to a cardiac sensor/stimulator. Each lead includes a lead body extending from one lead proximal end portion to one lead distal end portion. Each lead further includes at least three tissue sensing/stimulation electrodes disposed along the lead body and at least three terminal connections disposed along the lead proximal end. The tissue sensing/stimulation electrodes are each adapted to sense or stimulate a subject's heart. The cardiac sensor/stimulator includes a signal processing circuit adapted to sense the heart in a first instance and stimulate the heart in a second instance by way of one or more tissue electrode configurations. The configurations are selectable from any combination of the tissue sensing/stimulation electrodes of each implanted lead and an indifferent return electrode. In one example, the signal processing circuit automatically selects the tissue electrode configurations. In another example, a user (manually) selects the tissue electrode configurations.

12 Claims, 13 Drawing Sheets

| | | |
|---|---|---|
| 224 | OPTION 1 | 208A – 208B |
| 226 | OPTION 2 | 208A – 208C |
| 228 | OPTION 3 | 208A – 208D |
| 230 | OPTION 4 | 208A – 414 |
| 232 | OPTION 5 | 208A – 416 |
| 234 | OPTION 6 | 208B – 208C |
| 236 | OPTION 7 | 208B – 208D |
| 238 | OPTION 8 | 208B – 414 |
| 240 | OPTION 9 | 208B – 416 |
| 242 | OPTION 10 | 208C – 208D |
| 244 | OPTION 11 | 208C – 414 |
| 246 | OPTION 12 | 208C – 416 |
| 248 | OPTION 13 | 208D – 414 |
| 250 | OPTION 14 | 208D – 416 |
| 252 | OPTION 15 | 414 – 416 |

417

| | | |
|---|---|---|
| 418 | OPTION 1 | 208A1 – 208A2 |
| 419 | OPTION 2 | 208A1 – 208A3 |
| 420 | OPTION 3 | 208A1 – 208A4 |
| 421 | OPTION 4 | 208A1 – 208B1 |
| 422 | OPTION 5 | 208A1 – 208B2 |
| 423 | OPTION 6 | 208A1 – 208B3 |
| 424 | OPTION 7 | 208A1 – 208B4 |
| 425 | OPTION 8 | 208A1 – 414 |
| 426 | OPTION 9 | 208A1 – 416 |
| 427 | OPTION 10 | 208A2 – 208A3 |
| 428 | OPTION 11 | 208A2 – 208A4 |
| 429 | OPTION 12 | 208A2 – 208B1 |
| 430 | OPTION 13 | 208A2 – 208B2 |
| 431 | OPTION 14 | 208A2 – 208B3 |
| 432 | OPTION 15 | 208A2 – 208B4 |
| 433 | OPTION 16 | 208A2 – 414 |
| 434 | OPTION 17 | 208A2 – 416 |
| 435 | OPTION 18 | 208A3 – 208A4 |
| 436 | OPTION 19 | 208A3 – 208B1 |
| 437 | OPTION 20 | 208A3 – 208B2 |
| 438 | OPTION 21 | 208A3 – 208B3 |
| 439 | OPTION 22 | 208A3 – 208B4 |
| 440 | OPTION 23 | 208A3 – 414 |
| 441 | OPTION 24 | 208A3 – 416 |
| 442 | OPTION 25 | 208A4 – 208B1 |
| 443 | OPTION 26 | 208A4 – 208B2 |
| 444 | OPTION 27 | 208A4 – 208B3 |
| 445 | OPTION 28 | 208A4 – 208B4 |
| 446 | OPTION 29 | 208A4 – 414 |
| 447 | OPTION 30 | 208A4 – 416 |
| 448 | OPTION 31 | 208B1 – 208B2 |
| 449 | OPTION 32 | 208B1 – 208B3 |
| 450 | OPTION 33 | 208B1 – 208B4 |
| 451 | OPTION 34 | 208B1 – 414 |
| 452 | OPTION 35 | 208B1 – 416 |
| 453 | OPTION 36 | 208B2 – 208B3 |
| 454 | OPTION 37 | 208B2 – 208B4 |
| 455 | OPTION 38 | 208B2 – 414 |
| 456 | OPTION 39 | 208B2 – 416 |
| 457 | OPTION 40 | 208B3 – 208B4 |
| 458 | OPTION 41 | 208B3 – 414 |
| 459 | OPTION 42 | 208B3 – 416 |
| 460 | OPTION 43 | 208B4 – 424 |
| 461 | OPTION 44 | 208B4 – 416 |
| 462 | OPTION 45 | 414 – 416 |

| | | | | | |
|---|---|---|---|---|---|
| 506 | OPTION 1 | 208A1 - 208A2 | 551 | OPTION 46 | 208A4 - 416 |
| 507 | OPTION 2 | 208A1 - 208A3 | 552 | OPTION 47 | 208B1 - 208B2 |
| 508 | OPTION 3 | 208A1 - 208A4 | 553 | OPTION 48 | 208B1 - 208B3 |
| 509 | OPTION 4 | 208A1 - 208B1 | 554 | OPTION 49 | 208B1 - 208B4 |
| 510 | OPTION 5 | 208A1 - 208B2 | 555 | OPTION 50 | 208B1 - 208C1 |
| 511 | OPTION 6 | 208A1 - 208B3 | 556 | OPTION 51 | 208B1 - 208C2 |
| 512 | OPTION 7 | 208A1 - 208B4 | 557 | OPTION 52 | 208B1 - 208C3 |
| 513 | OPTION 8 | 208A1 - 208C1 | 558 | OPTION 53 | 208B1 - 208C4 |
| 514 | OPTION 9 | 208A1 - 208C2 | 559 | OPTION 54 | 208B1 - 414 |
| 515 | OPTION 10 | 208A1 - 208C3 | 560 | OPTION 55 | 208B1 - 416 |
| 516 | OPTION 11 | 208A1 - 208C4 | 561 | OPTION 56 | 208B2 - 208B3 |
| 517 | OPTION 12 | 208A1 - 414 | 562 | OPTION 57 | 208B2 - 208B4 |
| 518 | OPTION 13 | 208A1 - 416 | 563 | OPTION 58 | 208B2 - 208C1 |
| 519 | OPTION 14 | 208A2 - 208A3 | 564 | OPTION 59 | 208B2 - 208C2 |
| 520 | OPTION 15 | 208A2 - 208A4 | 565 | OPTION 60 | 208B2 - 208C3 |
| 521 | OPTION 16 | 208A2 - 208B1 | 566 | OPTION 61 | 208B2 - 208C4 |
| 522 | OPTION 17 | 208A2 - 208B2 | 567 | OPTION 62 | 208B2 - 414 |
| 523 | OPTION 18 | 208A2 - 208B3 | 568 | OPTION 63 | 208B2 - 416 |
| 524 | OPTION 19 | 208A2 - 208B4 | 569 | OPTION 64 | 208B3 - 208B4 |
| 525 | OPTION 20 | 208A2 - 208C1 | 570 | OPTION 65 | 208B3 - 208C1 |
| 526 | OPTION 21 | 208A2 - 208C2 | 571 | OPTION 66 | 208B3 - 208C2 |
| 527 | OPTION 22 | 208A2 - 208C3 | 572 | OPTION 67 | 208B3 - 208C3 |
| 528 | OPTION 23 | 208A2 - 208C4 | 573 | OPTION 68 | 208B3 - 208C4 |
| 529 | OPTION 24 | 208A2 - 414 | 574 | OPTION 69 | 208B3 - 414 |
| 530 | OPTION 25 | 208A2 - 416 | 575 | OPTION 70 | 208B3 - 416 |
| 531 | OPTION 26 | 208A3 - 208A4 | 576 | OPTION 71 | 208B4 - 208C1 |
| 532 | OPTION 27 | 208A3 - 208B1 | 577 | OPTION 72 | 208B4 - 208C2 |
| 533 | OPTION 28 | 208A3 - 208B2 | 578 | OPTION 73 | 208B4 - 208C3 |
| 534 | OPTION 29 | 208A3 - 208B3 | 579 | OPTION 74 | 208B4 - 208C4 |
| 535 | OPTION 30 | 208A3 - 208B4 | 580 | OPTION 75 | 208B4 - 414 |
| 536 | OPTION 31 | 208A3 - 208C1 | 581 | OPTION 76 | 208B4 - 416 |
| 537 | OPTION 32 | 208A3 - 208C2 | 582 | OPTION 77 | 208C1 - 208C2 |
| 538 | OPTION 33 | 208A3 - 208C3 | 583 | OPTION 78 | 208C1 - 208C3 |
| 539 | OPTION 34 | 208A3 - 208C4 | 584 | OPTION 79 | 208C1 - 208C4 |
| 540 | OPTION 35 | 208A3 - 414 | 585 | OPTION 80 | 208C1 - 414 |
| 541 | OPTION 36 | 208A3 - 416 | 586 | OPTION 81 | 208C1 - 416 |
| 542 | OPTION 37 | 208A4 - 208B1 | 587 | OPTION 82 | 208C2 - 208C3 |
| 543 | OPTION 38 | 208A4 - 208B2 | 588 | OPTION 83 | 208C2 - 208C4 |
| 544 | OPTION 39 | 208A4 - 208B3 | 589 | OPTION 84 | 208C2 - 414 |
| 545 | OPTION 40 | 208A4 - 208B4 | 590 | OPTION 85 | 208C2 - 416 |
| 546 | OPTION 41 | 208A4 - 208C1 | 591 | OPTION 86 | 208C3 - 208C4 |
| 547 | OPTION 42 | 208A4 - 208C2 | 592 | OPTION 87 | 208C3 - 414 |
| 548 | OPTION 43 | 208A4 - 208C3 | 593 | OPTION 88 | 208C3 - 416 |
| 549 | OPTION 44 | 208A4 - 208C4 | 594 | OPTION 89 | 208C4 - 414 |
| 550 | OPTION 45 | 208A4 - 414 | 595 | OPTION 90 | 208C4 - 416 |
| | | | 596 | OPTION 91 | 414 - 416 |

*FIG. 5B*

| 603 | | |
|---|---|---|
| 604 | OPTION 1 | 208C1 – 208C2 |
| 605 | OPTION 2 | 208C1 – 208C3 |
| 606 | OPTION 3 | 208C1 – 208C4 |
| 607 | OPTION 4 | 208C1 – 414 |
| 608 | OPTION 5 | 208C1 – 416 |
| 609 | OPTION 6 | 208C2 – 208C3 |
| 610 | OPTION 7 | 208C2 – 208C4 |
| 611 | OPTION 8 | 208C2 – 414 |
| 612 | OPTION 9 | 208C2 – 416 |
| 613 | OPTION 10 | 208C3 – 208C4 |
| 614 | OPTION 11 | 208C3 – 414 |
| 615 | OPTION 12 | 208C3 – 416 |
| 616 | OPTION 13 | 208C4 – 414 |
| 617 | OPTION 14 | 208C4 – 416 |
| 618 | OPTION 15 | 414 – 416 |

MULTI-SITE LEAD/SYSTEM USING A MULTI-POLE CONNECTION AND METHODS THEREFOR

TECHNICAL FIELD

This document pertains generally to cardiac sensing/stimulation systems, and more particularly, but not by way of limitation, to a multi-site lead/system using a multi-pole connection and methods therefor.

BACKGROUND

Tissue electrodes implanted in a body of a subject for electrical pacing, defibrillation, or cardioversion of a heart are known. More specifically, tissue electrodes implanted within, on, or about the heart have been used to reverse (i.e., defibrillate or cardiovert) certain life threatening arrhythmias (i.e., irregular heart rhythms), or to stimulate contraction (i.e., pacing) of the heart, where electrical energy is applied to the heart via the tissue electrodes to return the heart to normal rhythm. Tissue electrodes have also been used to sense cardiac activity, such as intrinsic or responsive signals of the heart. Tissue electrodes detect abnormally slow (referred to as "bradyarrhythmia") or abnormally fast (referred to as "tachyarrhythmia") heartbeats. In response to the sensed bradyarrhythmia or tachyarrhythmia condition, a cardiac sensor/stimulator device produces pacing or defibrillation pulses, respectively, to correct the condition.

The tissue electrodes' ability to sense, pace, defibrillate or cardiovert a subject's heart depends, in part, on the location of the electrodes within, on, or about the heart and the interface between the tissue electrodes and nearby heart tissue. Typically, the tissue electrodes are arranged on a lead body in two ways (or categories)—bipolar and unipolar arrangements. First, a bipolar arrangement includes a pair of tissue electrodes on the lead which form a single electrical circuit (i.e., one electrode is positive and one electrode is negative). Second, a unipolar arrangement includes one tissue electrode which represents one pole, while the other pole is represented by the cardiac sensor/stimulator device body or minute ventilation electrode. Through the use of unipolar and bipolar configured leads, the sensing, pacing, defibrillation or cardioversion is limited, sometimes to a heart location other than or different from the desired or optimum position.

Some subjects may require a sensing/stimulation system to detect and pace or shock an abnormal heart in more than one location in the cardiac region, wherein such locations are distant from one another. In such situations, the only solutions currently available are for a subject to have multiple individual leads or a lead with multiple lead proximal end portions (referred to as "legs") implanted within his/her thoracic cavity or elsewhere, one of the leads/legs for use in sensing activity or delivering stimulation to a first position and one or more other leads/legs for use in sensing activity or delivering stimulation to at least a second position.

Having multiple individual leads or having a lead with multiple lead proximal end portions implanted within the subject's thoracic cavity or elsewhere is undesirable for many reasons. For instance, the complexity and time involved in implanting multiple leads/legs is typically greater than the complexity and time needed to implant a single lead having one lead proximal end portion. In addition, multiple leads or lead legs may mechanically interact with one another after implantation in a negative fashion. As another example, as more leads are implanted within, on, or about the heart, the ability to add other leads is reduced. Similarly, as more lead legs are connected to a cardiac sensor/stimulator device, the device header must grow to accommodate the additional lead connector cavities. A further issue related to the implantation of multiple leads or lead legs is increased pocket bulk (i.e., more space/volume in the body(s) of implanted hardware).

Another problem of current leads, systems, and methods relates to the treatment of cardiovascular subjects experiencing congestive heart failure (referred to simply as "CHF"). CHF, which can result from a number of causes such as long-term hypertension, is a condition in which the muscle in the walls of at least one of the right and (more typically) the left side of the heart deteriorates resulting in, among other things, disynchronous heart rhythm and enlarging of the heart. Often times in subjects experiencing CHF, the left side of the heart does not beat at the same time as the right side causing the pumping action of the heart to be inefficient. Further, subjects experiencing CHF often develop enlarged hearts as a result of scarring or formation of deposits in the heart muscle. For reasons similar to those discussed above, currently available leads, systems, and methods may not provide the sensing, pacing, defibrillation or cardioversion that is needed to adequately or optimally treat CHF.

SUMMARY

A lead comprises a lead body extending from one lead proximal end portion to one lead distal end portion and having an intermediate portion therebetween. At least three tissue sensing/stimulation electrodes are disposed along the lead body, and at least three terminal connections are disposed along the lead proximal end portion. The at least three tissue sensing/stimulation electrodes are each adapted to sense or stimulate (i.e., pace, defibrillate, or cardiovert) a heart of a subject. At least three conductors are contained within the lead body and extend between the terminal connections and the tissue sensing/stimulation electrodes.

Several options for the lead are as follows. In one example, the tissue sensing/stimulation electrodes are configurable to sense in a first instance and stimulate in a second instance, each occurring by way of one or more tissue electrode configurations. In another example, the tissue electrode configurations are selectable, at least in part, from any combination of the tissue sensing/stimulation electrodes (including an electrical coupling of two or more electrodes) implanted within a subject. In yet another example, the lead body includes a stylet or guidewire receiving cavity therein, and at least one preformed biased portion adapted to return to a preformed shape upon removal of a stylet or a guidewire from the cavity.

A system comprises a cardiac sensor/stimulator (capable of sensing intrinsic or responsive heart activity or stimulating the heart) and at least one lead. Examples of the cardiac sensor/stimulator include, among other things, a pacemaker, a cardiac resynchronization therapy device, a defibrillator, and a pacing system analyzer. Each lead includes a lead body extending from one lead proximal end portion to one lead distal end portion and having three or more tissue sensing/stimulation electrodes adapted for sensing or stimulating a heart of a subject disposed therealong. The one lead proximal end portion is sized and shaped to couple to the cardiac sensor/stimulator thereby electrically connecting each of the tissue sensing/stimulation electrodes to a signal processing circuit of the cardiac sensor/stimulator. The signal processing circuit is adapted to sense the heart in a first instance and stimulate the heart in a second instance by way of one or more selected tissue electrode configurations.

Several options for the system are as follows. In one example, the signal processing circuit is adapted to select the one or more tissue electrode configurations from the tissue sensing/stimulation electrodes of each lead (including intralead and interlead combinations) and one or more indifferent return electrode associated with the cardiac sensor/stimulator. In another example, the signal processing circuit is adapted to select the one or more tissue electrode configurations using, at least in part, one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter. In yet another example, the system further comprises an external programmer including a telemetry device communicatively couplable to the signal processing circuit. The external programmer is adapted to receive a selection of the one or more tissue electrode configurations.

Other options for the system are as follows. In one example, the cardiac sensor/stimulator includes at least one multi-pole connector cavity sized and shaped to receive one lead proximal end portion. In another example, the selected tissue electrode configurations include at least one tissue sensing/stimulation electrode positioned to sense or stimulate one or both of a left side of the heart or a right side of the heart. In yet another example, the selected tissue electrode configurations include at least one tissue sensing/stimulation electrode positioned to sense or stimulate a left and right side of the heart. In a further example, the system further comprises one or a combination of a posture sensor, a blood flow sensor, a blood pressure sensor, an impedance sensor, a blood volume sensor, an acceleration or motion sensor, a spatial distance sensor, or a blood oxygen sensor. The sense devices may be coupled to the external programmer for storage, communication, or evaluation purposes.

A method of using a system comprises disposing portions of at least one lead within, on, or about a heart of a subject. One or more lead includes a lead body extending from one lead proximal end portion to one lead distal end portion and having three or more tissue sensing/stimulation electrodes disposed therealong. The method further comprises evaluating a plurality of tissue electrode configurations for each configuration's ability to sense or stimulate the heart. The plurality of tissue electrode configurations are generated from the tissue sensing/stimulation electrodes of each lead and one or more indifferent return electrode. Further yet, the method includes selecting one or more tissue electrode configurations for sensing or stimulation (e.g., pacing, defibrillation, or cardioversion) of the heart.

Several options for using the system are as follows. In one example, the system further comprises sensing the heart through the selected tissue electrode configurations. In another example, the system further comprises stimulating the heart through the selected tissue electrode configurations. In one such example, stimulating the heart includes sequentially stimulating one or more chambers of the heart. In another such example, stimulating the heart includes multi-chamber stimulation of the heart. In yet another example, the system further comprises sensing or stimulating the heart through the selected tissue electrode configurations which includes at least two tissue sensing/stimulation electrodes electrically combined (i.e., coupled together).

Other options for using the system are as follows. In one example, disposing portions of the at least one lead includes disposing portions of a first lead within, on, or about a left side of the heart, and disposing portions of a second lead within, on, or about a right side of the heart. In another example, evaluating the plurality of tissue electrode configurations includes, at least in part, determining one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter. In yet another example, selecting the one or more tissue electrode configurations includes using a signal processing circuit of a cardiac sensor/stimulator. In a further example, selecting the one or more tissue electrode configurations includes using a manual entered selection from a user. The method may further include monitoring and re-selecting the one or more tissue electrode configurations.

The leads, systems, and methods described herein overcome many deficiencies of current leads, systems, and methods. As one example, through the use of a lead having a lead body extending from one lead proximal end portion to one lead distal end portion and including three or more tissue sensing/stimulation electrodes axially spaced from one another therealong, the opportunity exists for a user (e.g., an implanting physician) or a cardiac sensor/stimulator itself to choose among numerous tissue electrode configurations for sensing or stimulating the heart. The numerous possible tissue electrode configurations allow the user or the cardiac sensor/stimulator to recurrently select one or more tissue electrode configurations which optimizes or provides an acceptable balance of one or a combination of a stimulation threshold parameter, a stimulation impedance parameter, a stimulation selection parameter (including reduction of phrenic nerve or diaphragmatic stimulation), a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter. As another example, the lead—by possessing three or more tissue sensing/stimulation electrodes—may overcome the need for the implanting physician to have to physically move the lead once implanted for effective electrode positioning.

Several other advantages of the leads, systems, and methods described herein are as follows. As one example, the lead can accommodate unique, varying heart anatomies due to its three or more tissue sensing/stimulation electrodes disposed along the lead body. As another example, the system is adapted to accommodate changes in tissue electrode/heart tissue interface and changes in heart rhythm, which may occur over time. As yet another example, the lead reduces the need for multiple leads to be implanted within, on, or about the subject's heart. These and other examples, aspects, advantages, and features of the present leads, systems, and methods will be set forth in part in the detailed description, which follows, and in part will become apparent to those skilled in the art by reference to the following description of the present leads, systems, methods, and drawings or by practice of the same.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in this patent document.

FIG. 4B is a chart illustrating possible tissue electrode configurations for use in sensing or stimulating a subject's heart using a lead and a cardiac sensor/stimulator, as constructed in accordance with at least one embodiment.

FIG. 5B is a chart illustrating possible tissue electrode configurations for use in sensing or stimulating a subject's heart using a lead and a cardiac sensor/stimulator, as constructed in accordance with at least one embodiment.

DETAILED DESCRIPTION

Figure 1:
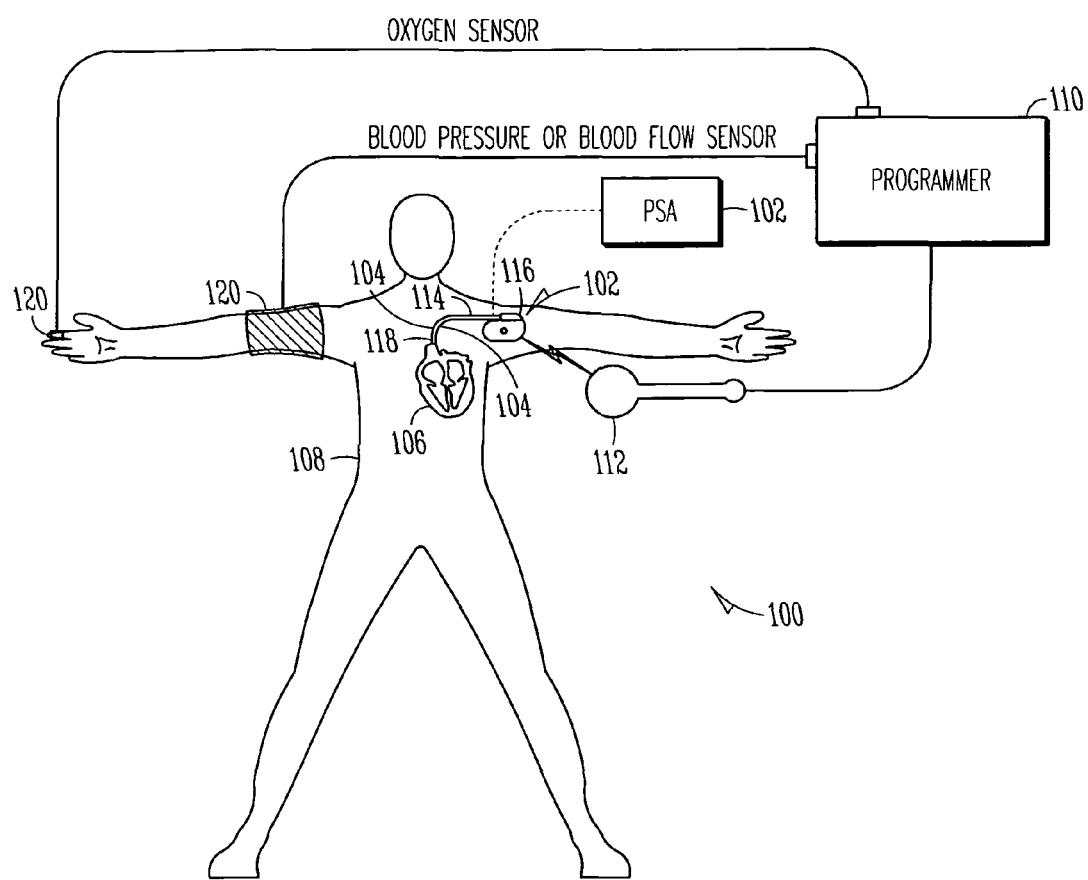
FIG. 1 is a schematic drawing illustrating portions of a system and an environment in which the system may be used, as constructed in accordance with at least one embodiment.

The following detailed description includes references to the accompanying drawings, which form a part of the detailed description. The drawings show, by way of illustration, specific embodiments in which the present leads, systems, and methods may be practiced. These embodiments, which are also referred to herein as "examples," are described in enough detail to enable those skilled in the art to practice the present leads, systems, and methods. The embodiments may be combined or varied, other embodiments may be utilized or structural, logical, or electrical changes may be made without departing from the scope of the present leads, systems, and methods. It is also to be understood that the various embodiments of the present leads, systems, and methods, although different, are not necessarily mutually exclusive. For example, a particular feature, structure or characteristic described in one embodiment may be included within other embodiments. The following detailed description is therefore, not to be taken in a limiting sense, and the scope of the present leads, systems, and methods are defined by the appended claims and their legal equivalents.

In this document the terms "a" or "an" are used to include one or more than One, and the term "or" is used to refer to a nonexclusive or, unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Leads, systems, and methods are provided herein for sensing or stimulating a heart of a subject by way of a lead having a lead body extending from one lead proximal end portion to one lead distal end portion and including three or more tissue sensing/stimulation electrodes disposed therealong. The leads, systems, and methods provide a user or a cardiac sensor/stimulator itself to choose among numerous possible tissue electrodes configurations for sensing or stimulating the heart. The numerous tissue electrode configurations allow the user or cardiac sensor/stimulator to recurrently select one or more tissue electrode configurations which optimizes one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter, all without having to physically move the lead after initial implantation.

FIG. 1 is a schematic drawing illustrating portions of a system 100 and an environment in which system 100 may be used. In FIG. 1, system 100 includes a cardiac sensor/stimulator 102, which is coupled via one or more leads 104 to a heart 106 of a human or other subject 108. Cardiac sensor/stimulator 102 may be implanted subcutaneously in subject's 108 chest, abdomen, or elsewhere or may be a device external to subject 108. In this example, system 100 also includes an external programmer 110 adapted to electrically communicate with cardiac sensor/stimulator 102, such as wirelessly through the use of a telemetry device 112. One or more internal or external sense devices 120 (e.g., a posture sensor, a blood flow sensor, a blood pressure sensor, an impedance sensor, a blood volume sensor, an acceleration or motion sensor, a spatial distance sensor, or a blood oxygen sensor) may be coupled (e.g., via USB-type or telemetry connections) to external programmer 110 to provide programmer 110 with many types of subject specific information (e.g., information related to the subject's blood-oxygen level, blood pressure or blood flow, etc.). Lead 104 includes one lead proximal end portion 114, which is coupled to cardiac sensor/stimulator 102 such as via a header 116, and one lead distal end portion 118, which is coupled within, on, or about portions of heart 106.

Cardiac sensor/stimulator 102 is intended to generically represent any type of generator for delivery of electrical stimulation (e.g., pacing, defibrillation, or cardioversion) to, or sensing intrinsic or responsive activity of, heart 106. Hence, cardiac sensor/stimulator 102 represents an example of, among other things, one or a combination of a pacemaker, a cardiac resynchronization therapy (referred to as "CRT") device, a defibrillator, a cardioverter, or a pacing system analyzer (referred to as "PSA").

In one example, cardiac sensor/stimulator 102 is a pacemaker. Pacemakers deliver timed sequences of low energy electrical stimuli, called pace pulses, to heart 106, such as via lead 104 having one or more tissue sensing/stimulation electrodes disposed within, on, or about heart 106. Heart 106 contractions are initiated in response to such pace pulses (this is referred to as "capturing" the heart). By properly timing the delivery of pace pulses, heart 106 can be induced to contract in proper rhythm, greatly improving its efficiency as a pump. Pacemakers are often used to treat subjects 108 with bradyarrhythmias, that is, hearts 106 that beat too slowly or irregularly. Pacemakers may also coordinate atrial and ventricular contractions to improve heart 106 pumping efficiency.

In another example, cardiac sensor/stimulator 102 is a CRT device for coordinating the spatial nature of heart 106 depolarizations for improving heart pumping efficiency, such as for subjects 108 experiencing CHF. In one such example, the CRT device may deliver appropriate timed pace pulses to different locations of the same heart 106 chamber to better coordinate the contraction of that heart chamber, or the CRT device may deliver appropriately timed pace pulses to different heart 106 chambers to improve the manner in which these different heart chambers contract together, such as to synchronize left and right side contractions.

In yet another example, cardiac sensor/stimulator 102 is a defibrillator that is capable of delivering higher energy electrical stimuli to heart 106 (as compared with, for example, pacing pulses). Defibrillators may include cardioverters, which synchronize the delivery of such stimuli to sensed intrinsic heart activity signals. Defibrillators are often used to treat subjects with tachyarrhythmias, that is, hearts 106 that beat too quickly. Such too-fast heart 106 rhythms cause diminished blood circulation because the heart isn't allowed sufficient time to fill with blood before contracting to expel the blood. Such pumping by heart 106 is inefficient. A defibrillator is capable of delivering a high energy electrical stimulus that is sometimes referred to as a defibrillation countershock, also referred to simply as a "shock." The countershock interrupts the tachyarrhythmia, allowing heart 106 to reestablish a normal rhythm for the efficient pumping of blood.

In a further example, cardiac sensor/stimulator 102 is a PSA. The PSA is a tester adapted to electrically connect to a lead proximal end portion 114, such as to one or more terminal connections 206 (FIG. 2A), for analyzing and verifying the performance of system 100. In addition, the PSA tester is typically equipped to sense the subject's 108 heart and to generate stimulation (e.g., pacing, defibrillation, or cardioversion) pulses as required to support subject 108 (FIG. 1) during the implantation process (e.g., of lead 104).

Figures 2A, 2B:
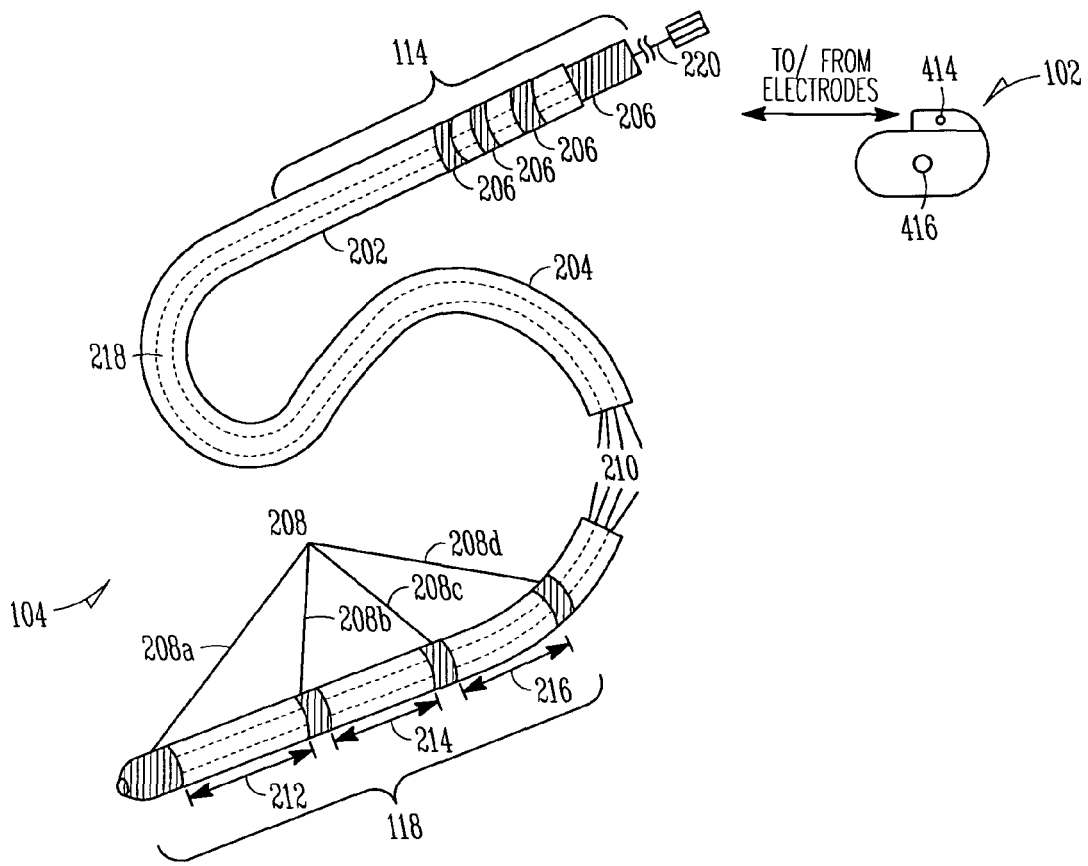
FIG. 2A is a perspective drawing illustrating a lead and a cardiac sensor/stimulator, as constructed in accordance with at least one embodiment.
FIG. 2B is a chart illustrating possible tissue electrode configurations for use in sensing or stimulating a subject's heart using a lead and a cardiac sensor/stimulator, as constructed in accordance with at least one embodiment.

FIG. 2A is a perspective drawing illustrating a lead 104 and a cardiac sensor/stimulator 102, according to at least one embodiment. Lead 104 includes a lead body 202 extending from one lead proximal end portion 114 to one lead distal end portion 118 and having an intermediate portion 204 therebetween. In one example, lead body 202 is composed of biocompatible tubing such as medical grade silicon rubber. As discussed in association with FIG. 1, a system 100 (FIG. 1) includes, among other things, lead 104 for electrically coupling cardiac sensor/stimulator 102 (see also FIG. 1) to a heart 106 (FIG. 1) for sensing intrinsic or responsive electrical heart activity or delivering electrical therapy, such as pacing stimulations or defibrillation countershock stimulations.

Referring again to FIG. 2A, the one lead proximal end portion 114 includes at least three terminal connections 206 disposed therealong. Similarly, the lead body 202 includes at least three tissue sensing/stimulation electrodes 208 (e.g., 208a, 208b, 208c, 208d) disposed therealong. Tissue sensing/stimulation electrodes 208 are each adapted to sense or stimulate heart 106 of subject 108 (FIG. 1) and are electrically coupled to terminal connections 206 via at least three conductors 210 contained within lead body 202. The one lead proximal end portion 114 and terminal connections 206 disposed therealong are sized and shaped to couple to a multi-pole connector cavity 402 (see, e.g., FIG. 4A), which may be incorporated into a header 116 (FIG. 1) of cardiac sensor/stimulator 102 (FIG. 1). It is through the coupling between lead proximal end portion 114 and multi-pole connector cavity 402 (FIG. 4A) that tissue sensing/stimulation electrodes 208 are electrically coupled to a signal processing circuit 302 (FIG. 3) of cardiac sensor/stimulator 102.

In the example of FIG. 2A, lead body 202 includes a stylet or guidewire receiving cavity 218, sized and shaped to receive a stylet 220 or a guidewire, therein. Stylet 220 may be used to stiffen lead 104 and is sized and shaped to facilitate the insertion of lead 104 into, for example, a coronary sinus of heart 106, a right atrium or ventricle of heart 106, or a left atrium or ventricle of heart 106. In one example, a stylet knob is coupled with stylet 220 for rotation of the same, advancing a conductor, or for manipulating lead 104.

Also shown in the example of FIG. 2A, tissue sensing/stimulation electrodes 208 are axially spaced from one another by one or more predetermined distances 212, 214, 216. The predetermined distances 212, 214, 216 between tissue sensing/stimulation electrodes 208 provide a plurality of tissue electrode configurations for sensing or stimulating the subject's heart 106 (FIG. 1). Options available for the one or more predetermined distances 212, 214, 216 are numerous. In one example, the predetermined distances range from 9-12 mm; however, the lead 104 described herein is not so limited, as the distances available are only confined by the longitudinal length of lead 104. Advantageously, predetermined distances 212, 214, 216 may be used to accommodate varying heart anatomies (i.e., sense or stimulate heart 106 at many locations), such as is common in subjects 108 (FIG. 1) experiencing CHF.

FIG. 2B is a chart 222 illustrating a plurality of tissue electrode configurations possible for sensing or stimulating a subject's heart 106 (FIG. 1) using a lead 104 (FIG. 2A) including three or more tissue sensing/stimulation electrodes 208 (FIG. 2A) and a cardiac sensor/stimulator 102. As mentioned above, tissue sensing/stimulation electrodes 208 are typically arranged on a lead body 202 (FIG. 2A) in one of two ways—a unipolar or bipolar arrangement. Accordingly, when viewed on an intralead basis, typical leads are limited to only a couple tissue electrode configurations with which to sense or stimulate across.

FIG. 2B illustrates at least fifteen tissue electrode configurations 224-252 possible for sensing or stimulating across with a lead 104 (FIG. 2A) having four tissue sensing/stimulation electrodes 208a, 208b, 208c, 208d (FIG. 2A). Beyond the fifteen tissue electrode configurations 224-252 shown in FIG. 2B, additional configurations, which include an electrical coupling of two or more tissue sensing/stimulation electrodes 208 are also possible. In one example, each tissue sensing/stimulation electrode 208 is adapted to sense the heart 106 in a first instance and deliver stimulation to the heart 106 in a second instance. In another example, as shown in FIG. 2A, each tissue electrode 208 may be spaced apart from one another by one or more predetermined distance 212, 214, 216. By way of predetermined distances 212, 214, 216 (FIG. 2A) between tissue sensing/stimulation electrodes 208a, 208b, 208c, 208d (FIG. 2A), the opportunity exists for a user (e.g., an implanting physician) or cardiac sensor/stimulator 102 (FIG. 1) itself to use various tissue electrode spacing for the benefit of a subject 108 via sensing or stimulation of his/her heart 106.

Figure 3:
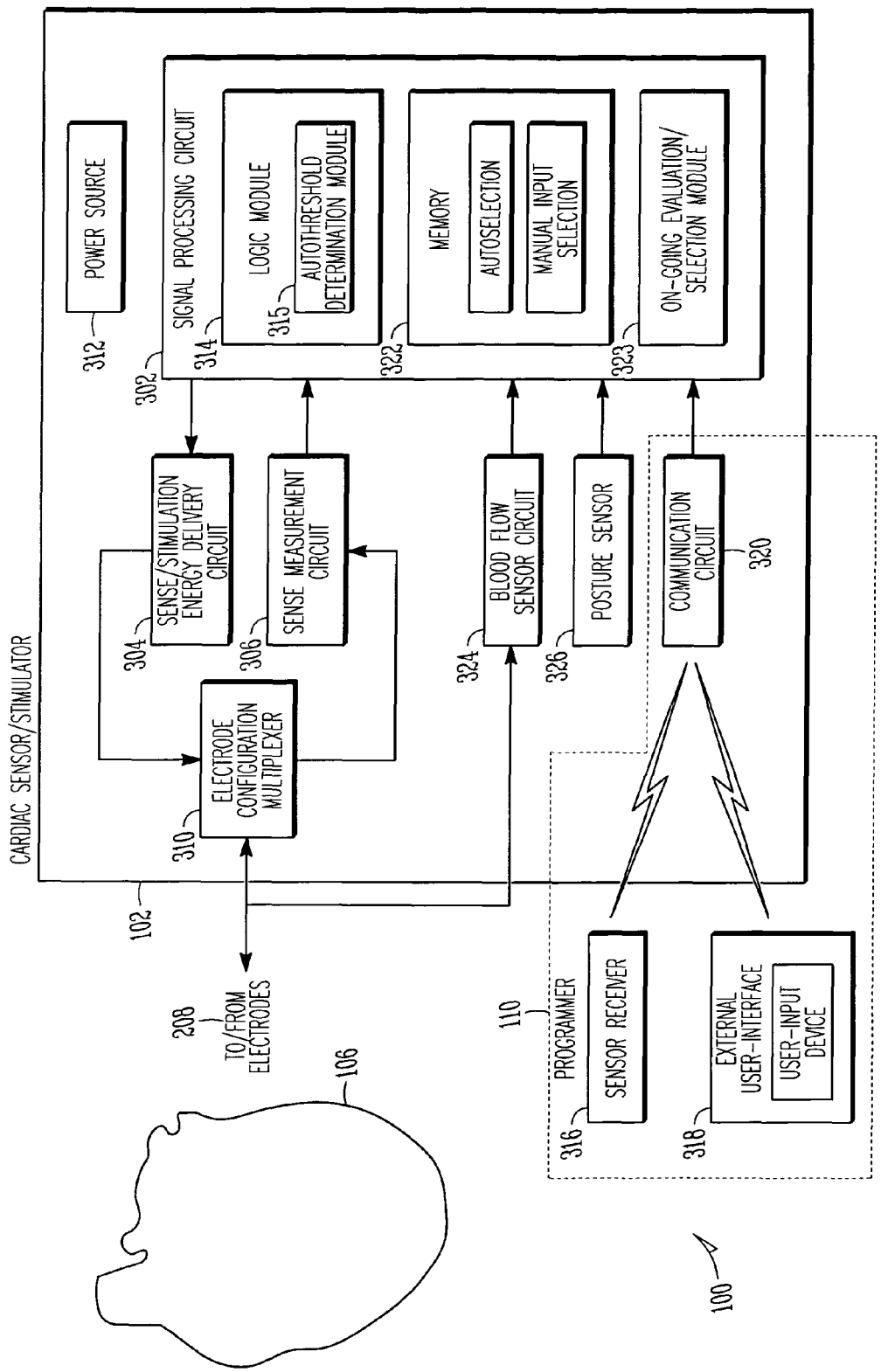
FIG. 3 is a schematic drawing illustrating portions of a system, including circuitry of a cardiac sensor/stimulator, as constructed in accordance with at least one embodiment.

FIG. 3 is a schematic drawing illustrating portions of a system 100 adapted to sense or stimulate (e.g., pace, defibrillate, or cardiovert) a heart 106 of a subject 108 (FIG. 1) at multiple locations within, on, or about the same. In the example shown, system 100 includes a hermetically sealed cardiac sensor/stimulator 102 and an external programmer 110. Cardiac sensor/stimulator 102 is connected to heart 106 by way of at least one lead 104 (FIGS. 1, 2A). In one example, lead 104 includes three or more tissue sensing/stimulation electrodes 208 adapted to sense or stimulate heart 106. Among other things, cardiac sensor/stimulator 102 includes a signal processing circuit 302, a sense/stimulation energy delivery circuit 304, a sense measurement circuit 306, an electrode configuration multiplexer 310, and a power source 312. Among other things, external programmer 110 includes an external/internal sensor receiver 316 and an external user-interface 318 including a user-input device. External/internal sensor receiver 316 is adapted to receive subject specific information from internal or external sensor(s) 120 (FIG. 1).

Figure 4A:
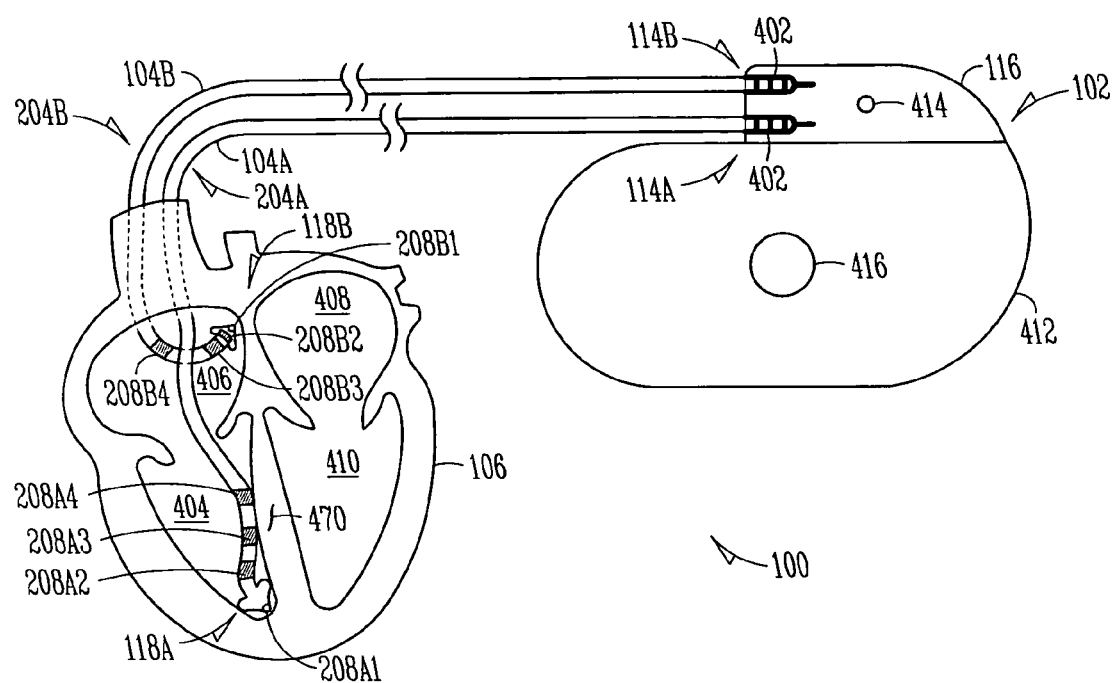
FIG. 4A is a schematic drawing illustrating at least one lead and a cardiac sensor/stimulator, as constructed in accordance with at least one embodiment.

Signal processing circuit 302 is adapted to sense heart 106 in a first instance and stimulate heart 106 in a second instance, each of which occur by way of one or more tissue electrode configurations selected from the three or more tissue sensing/stimulation electrodes 208 of each lead 104 (FIGS. 1, 2A) implanted within subject 108 (FIG. 1) (including intralead and interlead combinations) and one or more indifferent electrode (e.g., header electrode 414 or housing electrode 416-see, e.g., FIG. 4A). In one example, cardiac sensor/stimulator 102 (e.g., signal processing circuit 302) is adapted (i.e., programmed) to automatically analyze all possible tissue electrode configurations of system 100 and select the one or more tissue electrode configurations to be used in sensing or stimulating heart 106. Cardiac sensor/stimulator 102 may be further adapted (e.g., via an ongoing evaluation/selection module 323) to monitor and re-select the one or more tissue electrode configurations as necessary). In another example, programmer 110 is adapted (i.e., programmed) to automatically analyze all possible tissue electrode configurations of system 100 and select the one or more tissue electrode configurations to be used in sensing or stimulating heart 106. In yet another example, the one or more tissue electrode configurations used to sense or stimulate heart 106 is selected manually by a user (e.g., an implanting physician), and communicated to cardiac sensor/stimulator 102 (e.g., signal processing circuit 302) using a telemetry device 112 (FIG. 1) and a communication circuit 320 of cardiac sensor/stimulator 102. In the example shown, such automatic or manual selection of the one or more tissue electrode configurations is stored in a memory 322. In yet another example, the one or more tissue electrode configurations used to sense heart 106 in a first instance and stimulate heart 106 in a second instance are the same. In a further example, the one or more tissue electrode configurations used to sense heart 106 in a first instance and stimulate heart 106 in a second instance are different.

Figure 7:
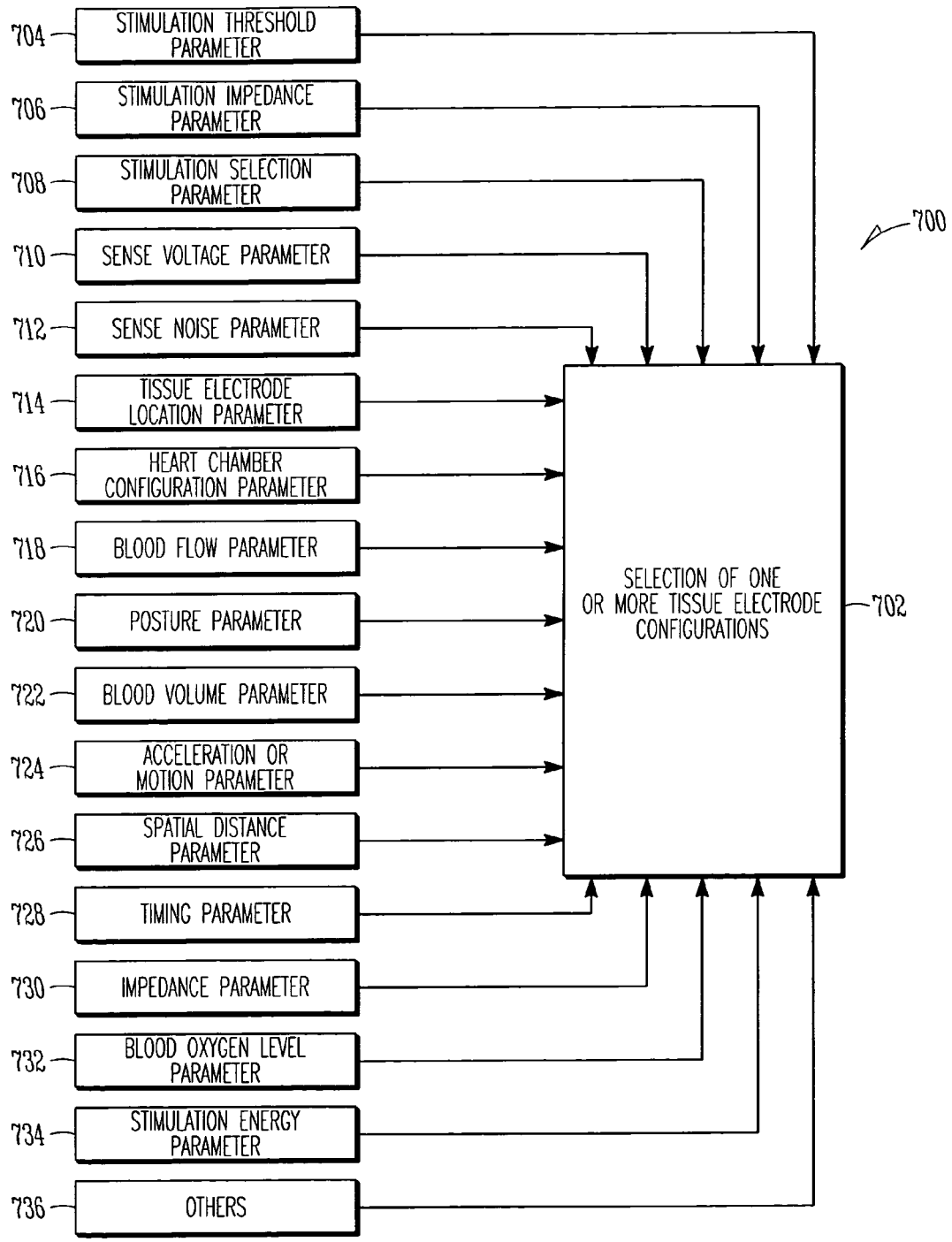
FIG. 7 is a chart illustrating various parameters, one or a combination of which may be used in a selection of one or more tissue electrode configurations for sensing or stimulating a heart of a subject, as constructed in accordance with at least one embodiment.

The one or more tissue electrode configurations may be selected (either automatically or manually) using, at least in part, one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter, all of which are further discussed below, such as in discussion of FIG. 7. In one example, at least one of the foregoing parameters are evaluated by way of a logic module 314 of signal processing circuit 302 and is used in the selection of the one or more tissue electrode configurations used to sense or stimulation heart 106.

As illustrated in the example of FIG. 3, cardiac sensor/stimulator 102 may include sense/stimulation energy delivery circuit 304 and sense measurement circuit 306 to sense intrinsic or responsive activity of (in the form of sense indication signals), and provide stimulation (e.g., pacing, defibrillation, or cardioversion) to, heart 106, respectively. In one such example, but not by way of limitation, sense/stimulation energy delivery circuit 304 delivers a pacing pulse stimulation via lead 104 (FIGS. 1, 2A) to one or more tissue sensing/stimulation electrode 208 located in a right ventricle of heart 106. Such pacing stimuli are usually delivered at a time when the particular heart chamber is in a relaxed, passive state and is being filled with blood. If the delivered pacing stimulus captures heart 106, myocardial (i.e., heart) tissue near the pacing site of tissue sensing/stimulation electrode(s) 208 begins to contract, which may be detected by sense measurement circuit 306. If the delivered pacing stimulus does not capture heart 106 (which may also be detected by sense measurement circuit 306), such tissue does not begin to contract. Similarly, defibrillation or cardioversion stock stimulation may also be applied to heart 106, with responsive heart 106 activity detected by sense measurement circuit 306. In addition, cardiac sensor/stimulator 102 may include electrode configuration multiplexer 310 to electrically connect cardiac sensor/stimulator 102 to the one or more selected tissue electrode configuration.

In this example, but as may vary, cardiac sensor/stimulator 102 further includes a blood flow sensor circuit 324 and a posture sensor 326. In one example, blood flow sensor circuit 324 is adapted to sense a blood flow signal indication of subject's 108 (FIG. 1) then-current blood flow. In another example, posture sensor 326 is adapted to sense a posture signal indicative of subject's 108 (FIG. 1) then-current posture orientation. A different posture signal is provided for different postures (i.e., a posture signal for upright postures differs from a posture signal for recumbent postures). One example of a suitable posture sensor 326 commercially available is a two-axis accelerometer, such as Model No. ADXL202E, manufactured by Analog Devices, Inc. of Norwood, Mass., USA; however, other posture sensors may also be used without departing from the scope of the leads, systems, and methods described herein. A history of both the blood flow signal and posture signal may be stored in memory 322 for use by system 100. Cardiac sensor/stimulator may further include a spatial analyzer adapted to communicate with, for example, an accelerometer in lead 104 (FIG. 1) to measure heart 106 contraction force. Cardiac sensor/stimulator 102 is powered by a power source 312, such as a battery.

FIG. 3 illustrates one conceptualization of various circuits, modules, and devices, which are implemented either in hardware or as one or more sequence of steps carried out on a (micro)processor or other controller. Such circuits, modules, and devices are illustrated separately for conceptual clarity; however, it is to be understood that the various circuits, modules, and devices of FIG. 3 need not be separately embodied, but may be combined or otherwise implemented, such as in hardware, software, or firmware. Although not shown in FIG. 3, cardiac sensor/stimulator 102, such as signal processing circuit 302, may further include amplification, demodulation, filter, analog-to-digital (A/D) conversion, digital-to-analog (D/A) conversion, and other circuits for extracting and storing information obtained through system 100.

Figure 5A:
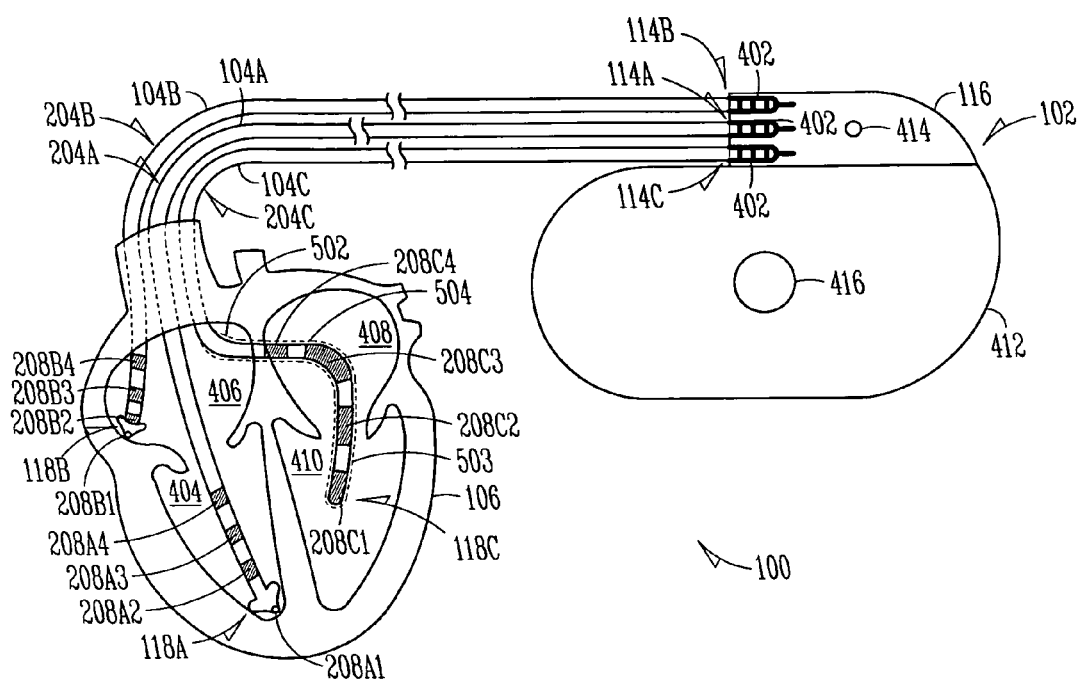
FIG. 5A is a schematic drawing illustrating at least one lead and a cardiac sensor/stimulator, as constructed in accordance with at least one embodiment.
Figures 6A, 6B:
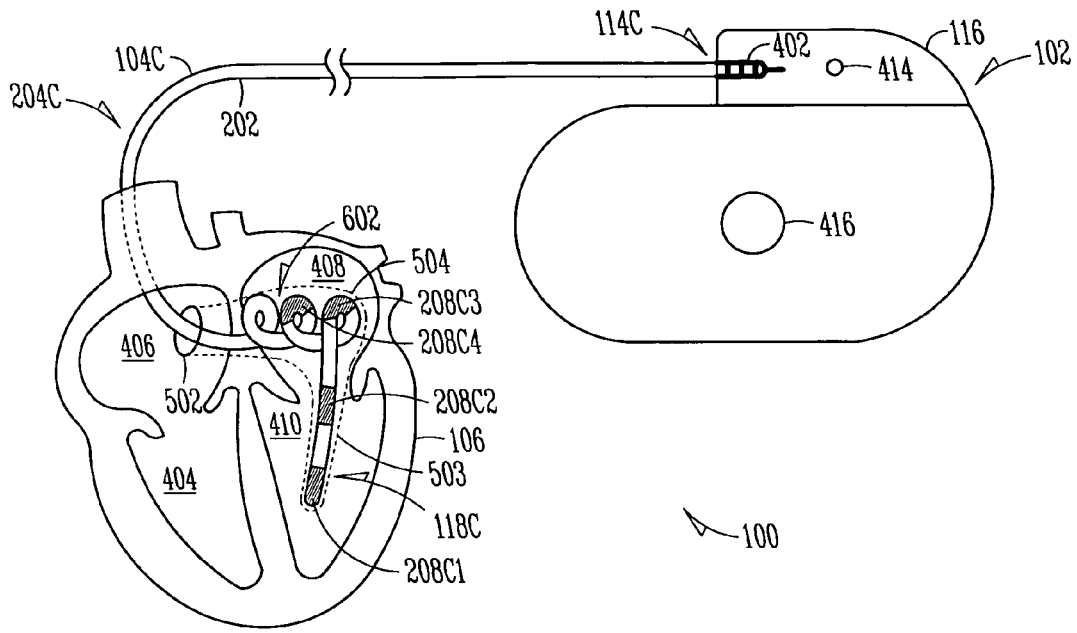
FIG. 6A is a schematic drawing illustrating at least one lead and a cardiac sensor/stimulator, as constructed in accordance with at least one embodiment.
FIG. 6B is a chart illustrating possible tissue electrode configurations for use in sensing or stimulating a subject's heart using a lead and a cardiac sensor/stimulator, as constructed in accordance with at least one embodiment.

FIGS. 4A, 5A, and 6A are schematic drawings illustrating various examples of portions of a system 100, including at least one lead 104 and a cardiac sensor/stimulator 102, as constructed in accordance with at least one embodiment. The lead(s) 104 couple cardiac sensor/stimulator 102 to a heart 106. In each example, lead 104 includes a lead body 202 (FIG. 2A) extending from one lead proximal end portion 114 to one lead distal end portion 118 and includes an intermediate portion 204 therebetween. Three or more tissue sensing/stimulation electrodes 208 are disposed along lead body 202 (FIG. 2A), while three or more terminal connections 206 (FIG. 2A) are disposed along lead proximal end portion 114. Tissue sensing/stimulation electrodes 208 are each adapted for sensing or stimulating (e.g., pacing, defibrillation, or cardioversion) of heart 106 of a subject 108 (FIG. 1).

As illustrated, each lead proximal end portion 114 is sized and shaped to couple to cardiac sensor/stimulator 102, such as a multi-pole connector cavity 402, thereby electrically connecting each of the tissue sensing/stimulation electrodes 208 to a signal processing circuit 302 (FIG. 3) of cardiac sensor/stimulator 102. In this example, each multi-pole connector cavity 402 is incorporated into a header 116 of cardiac sensor/stimulator 102, and is sized and shaped to receive the one lead proximal end portion 114. In another example (although not shown), multi-pole connector cavity 402 includes a housing (sized and shaped to receive the one lead proximal end portion 114) having at least one protective terminal contact device and a securing contact device thereby allowing electrical contact to be made between the tissue sensing/stimulation electrodes 208 and the signal processing circuit 302 (FIG. 3). This latter example is further described in Hoecke, et al., U.S. application Ser. No. 11/127,886, entitled "LEAD TERMINAL MULTI-TOOL," assigned to Cardiac Pacemakers, Inc., and hereby incorporated by reference in its entirety.

As discussed above, signal processing circuit 302 (FIG. 3) is adapted (i.e., programmed) to sense heart 106 in a first instance and stimulate heart 106 in a second instance, each occurring by way of one or more selected tissue electrode configurations. The one or more tissue electrode configurations are selected from the three or more tissue sensing/stimulation electrodes 208 of each lead 104 implanted within subject 108 (FIG. 1) (including intralead and interlead combinations) and one or more indifferent return electrode associated with cardiac sensor/stimulator (e.g., header electrode 414 or housing electrode 416).

In FIG. 4A, a schematic drawing of one example of portions of at least one lead 104A, 104B and cardiac sensor/stimulator 102 are shown, with the one lead distal end portion 118A of lead 104A being disposed in right ventricle 404 of heart 106 and with the one lead distal end portion 118B of lead 104B being disposed in right atrium 406 of heart 106. Left atrium 408 and left ventricle 410 are also illustrated. Lead distal end portion 118A of lead 104A includes three or more tissue sensing/stimulation electrodes, such as four tissue electrodes 208A1, 208A2, 208A3, and 208A4. Each electrode 208A1, 208A2, 208A3, 208A4 is electrically coupled to cardiac sensor/stimulator 102 by a conductor 210 (FIG. 2A) in lead 104A and is adapted to sense or stimulate (e.g., pace, defibrillate, or cardiovert) right ventricle 404 of heart 106. Similarly, lead distal end portion 118B of lead 104B includes three or more tissue sensing/stimulation electrodes, such as four tissue electrodes 208B1, 208B2, 208B3, and 208B4. Each electrode 208B1, 208B2, 208B3, 208B4 is electrically coupled to cardiac sensor/stimulator 102 by a conductor 210 (FIG. 2A) in lead 104B and is adapted to sense or stimulate (e.g., pace, defibrillate, or cardiovert) right atrium 406 of heart 106. In one example, lead 104A includes at least one preformed biased portion to urge one or more of the electrodes thereon against a septal wall 470 for pacing of the same.

Referring again to FIG. 4A, lead proximal end portions 114A, 114B of leads 104A, 104B, respectively, are coupled to cardiac sensor/stimulator 102 via multi-pole connector cavities 402 of header 116, which is affixed to a hermetically sealed housing 412. Hermetically sealed housing 412 may be formed from a conductive metal, such as titanium, and carries electronic components (i.e., circuits, modules, and devices) of cardiac sensor/stimulator 102 (see, e.g., FIG. 3). In this example, header 116 includes an indifferent header electrode 414 and housing 412 includes an indifferent housing electrode 416.

FIG. 5A is a schematic drawing, similar to FIG. 4A, illustrating another example of portions of at least one lead 104A, 104B, 104C coupling heart 106 and cardiac sensor/stimulator 102. In this example, system 100 includes a third lead 104C, the one lead distal end 118C of which is transvenously guided through the right atrium 406, into or through a coronary sinus ostium 502 and coronary sinus 504, or into a cardiac vein 503. Lead distal end portion 118C of lead 104C includes three or more tissue sensing/stimulation electrodes, such as four tissue electrodes 208C1, 208C2, 208C3, and 208C4. Each electrode 208C1, 208C2, 208C3, 208C4 is electrically coupled to cardiac sensor/stimulator 102 by a conductor 210 (FIG. 2A) in lead 104C and is adapted to sense or stimulate (e.g., pace, defibrillate, or cardiovert) the left side (i.e., left atrium 408 or left ventricle 410) of heart 106, which is useful for treatment of CHF or other cardiac disorders requiring therapy delivered to the left side of heart 106. In this example, at least one tissue electrode 208C1-C4 is positioned to sense or stimulate a left side (i.e., left atrium 408 or left ventricle 410) of heart 106 and at least one tissue electrode 208A1-A4, 208B1-B4 is positioned to sense or stimulate a right side (i.e., right ventricle 404 or right atrium 406) of heart 106. In this example, header 116 includes an indifferent header electrode 414 and housing 412 includes an indifferent housing electrode 416.

FIG. 6A is a schematic drawing illustrating another example of portions of at least one lead 104C coupling heart 106 and cardiac sensor/stimulator 102. In this example, system 100 includes a lead 104C, the one lead distal end 118C of which is transvenously guided through right atrium 406, into or through the coronary sinus ostium 502 and coronary sinus 504, or into a cardiac vein 503. Lead distal end portion 118C of lead 104C includes three or more tissue sensing/stimulation electrodes, such as four tissue electrodes 208C1, 208C2, 208C3, and 208C4. Each electrode 208C1, 208C2, 208C3, 208C4 is electrically coupled to cardiac sensor/stimulator 102 by a conductor 210 (FIG. 2A) in lead 104C and is adapted to sense or stimulate (e.g., pace, defibrillate, or cardiovert) a left side (i.e., left atrium 408 or left ventricle 410) of heart 106. This example disposition of lead 104C is useful for sensing or delivering stimulation energy to the left side of heart 106, such as for treatment of CHF or other cardiac disorders requiring therapy delivered to the left side of heart 106. In this example, header 116 includes an indifferent header electrode 414 and housing 412 includes an indifferent housing electrode 416.

Although not shown in FIG. 4A, 5A, or 6A, other dispositions of the one lead distal end 118 of lead 104 within, on, or about heart 106 are also possible. In one example, at least one lead distal end 118 is transarterially inserted into left atrium 408 or left ventricle 410. In another example, at least one lead distal end 118 is inserted into a pulmonary outflow tract of heart 106. In yet another example, at least one lead distal end 118 is implanted epicardially (i.e., attached to an outer surface of heart 106). In sum, the leads, systems, and methods described herein are adapted to work in a variety of electrode configurations and with a variety of electrical contacts or electrodes.

Referring again to FIG. 6A, a lead body 202 including at least one preformed biased portion is shown. In one example, lead body 202 is composed of a biocompatible material (e.g., polyether polyurethane) having shape memory characteristics such that it will return to its preformed shape once implanted and a stylet 220 (FIG. 2A) or a guidewire is removed from a stylet or guidewire receiving cavity 218 (FIG. 2A) disposed within lead body 202. In this example, lead body 202 has a helical preformed biased portion 602 near the one lead distal end portion 118C. Helical portion 602 includes a three-dimensional bias adapted to urge at least a portion of lead body 202 or electrode(s) 208C1, 208C2, 208C3, or 208C4 against a wall of a passage, such as a wall of coronary sinus 504. Helical portion 602 of lead body 202 provides lead 104C/vessel wall area interface to produce reliable, long term stability. In addition, helical portion 602 produces subtle lateral forces between electrodes 208C1, 208C2, 208C3, or 208C4 and adjacent vessel wall, resulting in low stimulation thresholds. In another example, the at least one preformed biased portion includes a curved portion, such as a sinusoidal curve.

FIGS. 4B, 5B, and 6B are charts illustrating possible tissue electrode configurations for use in sensing or stimulating a subject's heart using the systems 100 shown in FIGS. 4A, 5A, and 6A, respectively. Beyond the tissue electrode configurations shown in FIGS. 4A, 5A, and 6A, additional configurations/permutations, which include an electrical coupling of two or more tissue sensing/stimulation electrodes 208 are also possible. Programming of cardiac sensor/stimulator 102 or external programmer 110 may be written to first analyze the most probable optimal or acceptable configurations based on implant data or type of therapy needed by subject 108 (FIG. 1).

FIG. 4B is a chart 417 illustrating at least forty-five tissue electrode configurations 418-462 made possible by system 100 shown in FIG. 4A for sensing or stimulating a subject's heart 106 (FIG. 1). As discussed above, system 100 of FIG. 4A includes two leads 104A, 104B, each having four tissue sensing/stimulation electrodes 208A1, 208A2, 208A3, 208A4 and 208B1, 208B2, 208B3, 208B4, respectively, and a cardiac sensor/stimulator 102 having two indifferent electrodes 414, 416 associated therewith.

FIG. 5B is a chart 505 illustrating at least ninety-one tissue electrode configurations 506-596 made possible by system 100 shown in FIG. 5A for sensing or stimulating a subject's heart 106 (FIG. 1). As discussed above, system 100 of FIG. 5A includes three leads 104A, 104B, 104C, each having four tissue sensing/stimulation electrodes 208A1, 208A2, 208A3, 208A4; 208B1, 208B2, 208B3, 208B4; and 208C1, 208C2, 208C3, 208C4, respectively, and a cardiac sensor/stimulator 102 having two indifferent electrodes 414, 416 associated therewith.

FIG. 6B is a chart 603 illustrating at least fifteen tissue electrode configurations 604-618 made possible by system 100 shown in FIG. 6A for sensing or stimulating a subject's heart 106 (FIG. 1). As discussed above, system 100 of FIG. 6A includes one lead 104C having four tissue sensing/stimulation electrodes 208C1, 208C2, 208C3, 208C4 disposed thereon and a cardiac sensor/stimulator 102 having two indifferent electrodes 414, 416 associated therewith.

As discussed also above, signal processing circuit 302 (FIG. 3) of cardiac sensor/stimulator 102 is adapted to sense heart 106 in a first instance and stimulate (e.g., pace, defibrillate, or cardiovert) heart 106 in a second instance, each by way of one or more tissue selected electrode configurations. Advantageously, the leads, systems, and methods described herein allow the one or more tissue electrode configurations to be selected from various combinations of the tissue sensing/stimulation electrodes 208 of each lead 104 and one or more indifferent return electrode associated with cardiac sensor/stimulator 102 (e.g., header electrode 414 or housing electrode 416). In one example, the selected tissue electrode configurations include an intralead combination. In another example, the one or more selected tissue electrode configurations include an interlead combination. In yet another example, the one or more selected tissue electrode configurations include an electrical coupling of two or more tissue sensing/stimulation electrodes 208.

Selection of the one or more tissue electrode configurations used to sense or stimulate heart 106 of subject 108 may be done automatically (e.g., by cardiac sensor/stimulator 102 or external programmer 110) or manually by a user (e.g., an implanting physician), the latter of which may be communicated to cardiac sensor/stimulator 102 by way of a telemetry device 112 (FIG. 1) and a communication circuit 320 (FIG. 3). Among other things, selection of the one or more tissue electrode configurations may use one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter.

FIG. 7 is a chart 700 illustrating a variety of parameters 704-736, one or a combination of which may be used in a selection 702 of one or more tissue electrode configurations for sensing or stimulating a heart 106 (FIG. 1) of a subject 108 (FIG. 1). Selection 702 of the one or more tissue electrode configurations includes choosing the one or more tissue electrode configurations which (collectively) optimizes or provides an acceptable balance of one or a combination of parameters 704-736. In one example, selection 702 of the one or more tissue electrode configurations includes weighing at least one of parameters 704-736.

In one example, a stimulation threshold parameter 704 in combination with an acceleration or motion parameter 724 are used in selection 702 of the one or more tissue electrode configurations for stimulating heart 106 (FIG. 1). In varying examples, some or all possible tissue electrode configurations are or may be evaluated to determine which one or more configurations (optimally or acceptably) require the lowest amount of output energy (i.e., stimulation pulse or shock) be applied to heart 106 (FIG. 1) to capture the same. In one such example, capturing of heart 106 is determined by monitoring movement of at least one of the right atrium 406, the right ventricle 404, the left atrium 408, or the left ventricle 410 in response to a stimulation pulse or shock of predetermined amplitude. Motion may be determined by an ultrasound, an accelerometer, or the like. The presence or absence of such movement during an appropriate time period following the stimulation pulse or shock indicates a resulting capture and no capture, respectively.

Advantageously, by providing a system 100 (FIG. 1) adapted to determine to which one or more tissue electrode configurations require the lowest amount of energy be delivered while still ensuring reliable capture of heart 106 (FIG. 1), the life of a cardiac sensor/stimulator 102 (FIG. 1) may be prolonged, thereby minimizing the risk and expense to subject 108 (FIG. 1) associated with early explantation and replacement of cardiac sensor/stimulator 102 (FIG. 1). In one example, system 100 (FIG. 1) includes an autothreshold determination module 315 (FIG. 3) adapted to automatically determine whether a stimulation pulse or shock delivered through a first tissue electrode configuration has evoked a desired response from heart 106 (FIG. 1), and if not, testing a second, third, . . . , etc. tissue electrode configuration for the desired heart 106 (FIG. 1) response.

In another example, a stimulation impedance parameter 706 is used in selection 702 of the one or more tissue electrode configurations for stimulating heart 106 (FIG. 1). In varying examples, some or all possible tissue electrode configurations are or may be evaluated to determine which one or more configurations (optimally or acceptably) possess the lowest impedance at a tissue electrode 208 (FIG. 2A)/heart tissue 106 (FIG. 1) interface. Advantageously, by providing a system 100 (FIG. 1) adapted to determine which one or more tissue electrode configurations 208 (FIG. 2A) possesses the best heart tissue 206 contact, the life of cardiac sensor/stimulator 102 (FIG. 1) may be prolonged as result of less battery drain from stimulating heart 106.

In another example, a stimulation selection parameter 708 is used in selection 702 of the one or more tissue electrode configurations for stimulating heart 106 (FIG. 1). In varying examples, some or all possible tissue electrode configurations are or may be evaluated to determine which one or more configurations (optimally or acceptably) provides appropriate therapy to one or more chambers of heart 106 while minimizing phrenic nerve or diaphragmatic stimulation. Advantageously, by providing a system 100 (FIG. 1) adapted to determine which one or more tissue electrode configurations provides an appropriate balance between pulse or shock stimulation to heart 106 while minimizing phrenic nerve or diaphragmatic stimulation ensures subject 108 does not experience undesirable side effects.

In another example, a sense voltage parameter 710 is used in selection 702 of the one or more tissue electrode configurations for sensing heart 106 (FIG. 1). In varying examples, some or all possible tissue electrode configurations are or may be evaluated to determine which one or more configurations (optimally or acceptably) sense the greatest therapy response from heart 106 (FIG. 1). In another example, a sense noise parameter 712 is used in selection 702 of the one or more tissue electrode configurations for sensing heart 106 (FIG. 1). In varying examples, some or all possible tissue electrode configurations are or may be evaluated to determine which one or more configurations (optimally or acceptably) sense the therapy response from heart 106 (FIG. 1) with the lowest amount of noise. Advantageously, by providing a system 100 (FIG. 1) adapted to determine which one or more tissue electrode configurations senses the therapy response from heart 106 (FIG. 1) with the lowest amount of noise, greater amplitude of the sense indication signal and avoidance of inappropriate application of therapy results.

In another example, a tissue electrode location parameter 714 is used in selection 702 of the one or more tissue electrode configurations for sensing or stimulating heart 106 (FIG. 1). In varying examples, some or all possible tissue electrode configurations are or may be evaluated to determine which one or more configurations (optimally or acceptably) are positioned as needed for the appropriate therapy to be applied to heart 106 (FIG. 1) of subject 108 (FIG. 1). As one example, CHF typically results in the left atrium and left ventricle becoming enlarged and therefore requires that therapy (i.e., stimulation) be delivered to the left side of heart 106 (FIG. 1).

In yet another example, a heart chamber configuration parameter 716 is used in selection 702 of the one or more tissue electrode configurations for stimulating heart 106 (FIG. 1). In varying examples, some or all possible tissue electrode configurations are or may be evaluated to determine which one or more configurations (optimally or acceptably) allow for sequential or multi-chamber (e.g., four-chamber) stimulation of heart 106 (FIG. 1). In still another example, a blood flow parameter 718 is used in selection 702 of the one or more tissue electrode configurations for stimulating heart 106 (FIG. 1). In varying examples, some or all possible tissue electrode configurations are or may be evaluated to determine which one or more configurations (optimally or acceptably) result in beneficial hemodynamics (e.g., higher ejection fraction) from stimulation of heart 106 (FIG. 1).

In a further example, a posture parameter 720 is used (e.g., indirectly) in selection 702 of the one or more tissue electrode configurations for sensing or stimulating heart 106 (FIG. 1). Among other things, posture changes may affect an amount of fluid within a subject's thoracic region or a location of one or more tissue electrode 208 (FIG. 2A) in heart 106 (FIG. 1) (both of which may change evaluation of, for example, stimulation impedance parameter 706 or diaphragmatic/phrenic nerve stimulation). Accordingly, posture parameter 720 may be used to normalize evaluations of the one or more tissue electrode configurations which have occurred at different thoracic orientations and thereby play a role in selection 702 of the one or more tissue electrode configurations.

Other parameters that may be used in the selection 702 of one or more tissue electrode configurations include a blood volume parameter 722, an acceleration or motion parameter 724 or spatial distance parameter 726 (e.g., to measure contract force of heart 106), a timing parameter 728, an impedance parameter 730 (e.g., as measured between a minute ventilation electrode and tissue/sensing electrodes 208), a blood oxygen parameter 732, a stimulation energy parameter 734, or other parameter 736 know in the art to be of use when selecting a tissue electrode configuration. Moreover, selection 702 may include preventing detrimental heart remodeling or increasing beneficial heart remodeling.

Figure 8:
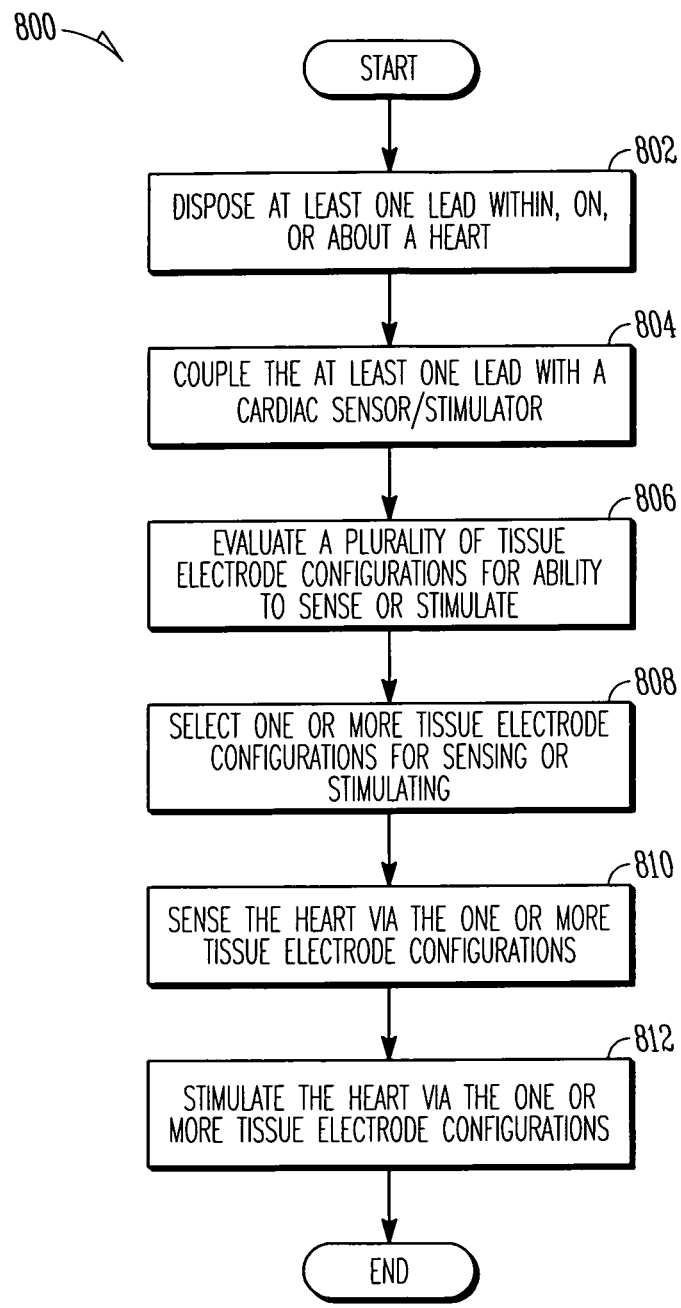
FIG. 8 is a flow chart illustrating a method of using a system, as constructed in accordance with at least one embodiment.

FIG. 8 is a flow chart illustrating a method 800 of using a system for sensing or stimulating a heart of a subject. At 802, portions of at least one lead are disposed within, on, or about a heart of a subject. Each lead includes a lead body extending from one lead proximal end portion to one lead distal end portion and having three or more tissue sensing/stimulation electrodes disposed therealong. In one example, at least one lead is disposed within, on, or about a right side (i.e., the right atrium or right ventricle) of the subject's heart. In another example, at least one lead is disposed within, on, or about a left side (i.e., the left atrium or left ventricle) of the subject's heart. In yet another example, at least one lead is disposed within, on, or about a septal wall of the heart or a pulmonary outflow tract of the heart.

At 804, the one lead proximal end portion of each lead is coupled with a cardiac sensor/stimulator. The coupling between the lead and the cardiac sensor/stimulator may include inserting each lead proximal end portion into a multi-pole connector cavity incorporated into a header of the cardiac sensor/stimulator. In one example, each lead proximal end portion is not coupled to the cardiac sensor/stimulator until after a user manually evaluates 806 a plurality of possible tissue electrode configurations.

At 806, the plurality of possible tissue electrode configurations is evaluated for each configuration's ability to sense or stimulate the subject's heart. The plurality of tissue electrode configurations are generated from the tissue sensing/stimulation electrodes of each lead and one or more indifferent return electrode associated with the cardiac sensor/stimulator (i.e., the configurations may be generated from intralead, interlead, or indifferent return electrode combinations). In one example, the plurality of tissue electrode configurations are evaluated using, at least in part, one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter. In another example, the plurality of tissue electrode configurations are evaluated manually by a user (e.g., an implanting physician). In yet another example, the plurality of tissue electrode configurations are automatically evaluated by the cardiac sensor/stimulator itself after being coupled with the lead proximal end portion.

At 808, one or more tissue electrode configurations for sensing or stimulating the subject's heart are selected. The selected configurations may include any combination of electrodes, including two or more tissue sensing/stimulation electrodes electrically combined (i.e., coupled together) for the purpose of lowering electrical impedance, achieving a lower stimulation threshold, increasing sense amplitude, or reducing phrenic/diaphragmatic stimulation or other undesirable side effects. In one example, the selection of the one or more tissue electrode configurations uses a manual selection from the implanting physician or other user, which is entered into an external user-interface of an external programmer and communicated to the cardiac sensor/stimulator via telemetry. In another example, the selection of the one or more tissue electrode configurations includes using a signal processing circuit of the cardiac sensor/stimulator. In yet another example, the system is adapted to recurrently evaluate 806 the plurality of possible tissue electrode configurations for each configuration's ability to sense or stimulate the heart and thereafter reselect 808 the optimal or acceptable tissue electrode configuration to use in sensing or stimulating.

At 810, the subject's heart is sensed through the selected tissue electrode configurations. By way of the selected tissue electrode configurations for sensing, a sense indication signal is obtained and communicated to the signal processing circuit for determination of corrective therapy (e.g., pacing, defibrillation, or cardioversion) to be applied to the subject. At 812, the subject's heart is stimulated (e.g., paced, defibrillated, or cardioverted) through the selected tissue electrode configurations for therapy delivery. In one example, stimulation applied to the heart is based on the sense indication signal received from the heart. In another example, the stimulation applied to the heart includes sequential stimulation of one or more chambers of the heart. In yet another example, the stimulation applied to the heart includes multi-chamber stimulation of the heart. In a further example, the tissue electrode configuration selected for sensing the heart is the same as the tissue electrode configuration selected for stimulating the heart. In yet a further example, the tissue electrode configuration selected for sensing the heart differs from the tissue electrode configuration selected for stimulating the heart.

Figure 9:
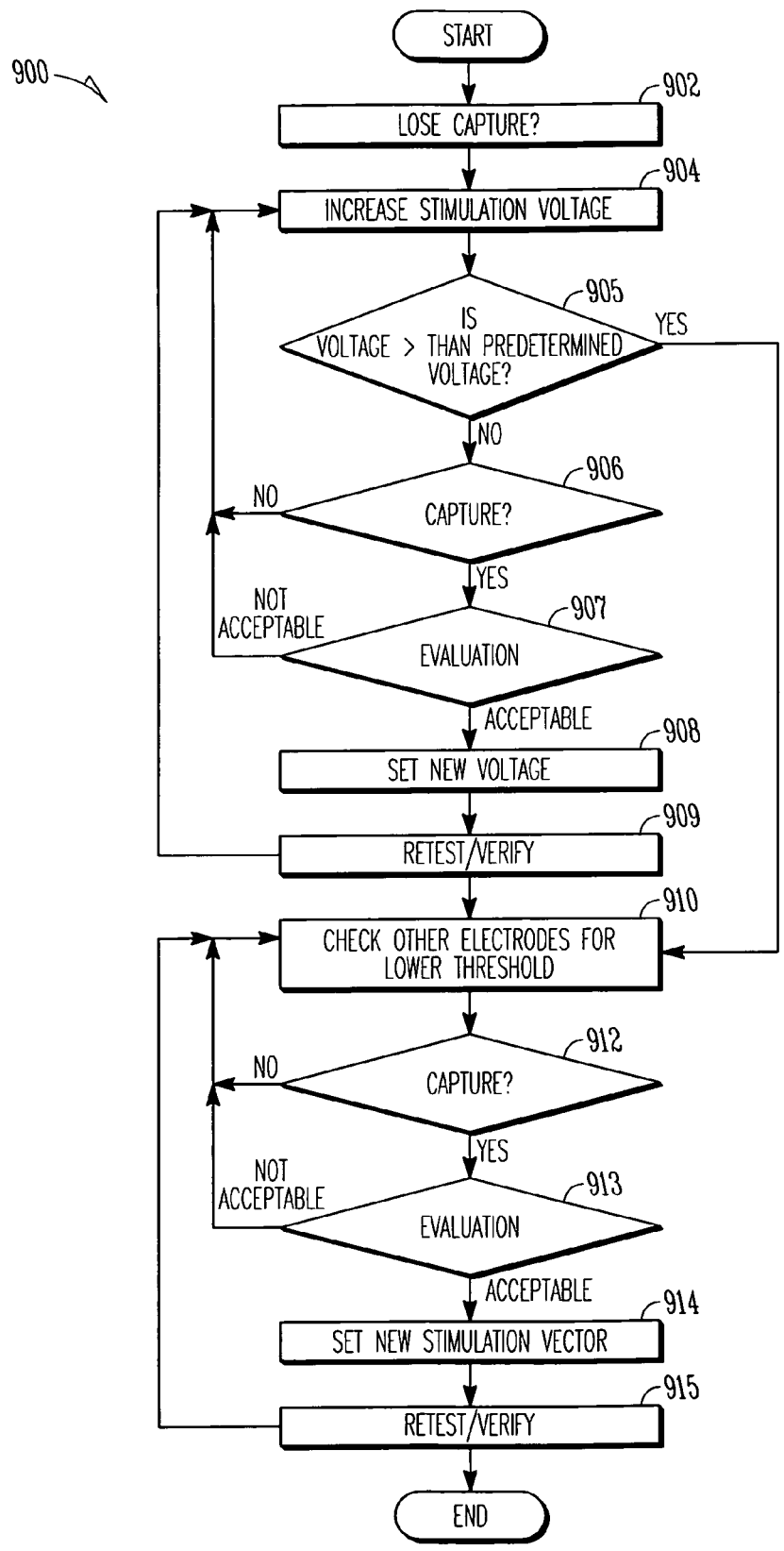
FIG. 9 is a flow chart illustrating another method of using a system, as constructed in accordance with at least one embodiment.

FIG. 9 is a flow chart illustrating a method 900 for regaining capture of a heart after it is lost as a result of, among other things, a myocardial infraction or micro-dislodgement of a lead. At 902, it is determined whether or not capture of the heart is lost. If capture is lost, a stimulation voltage is increased at 904. At 905, the increased stimulation voltage is compared with a predetermined voltage threshold. If the increased stimulation voltage is greater than (or in some cases, substantially equal to) the predetermined voltage threshold, a new (i.e., a different) set of tissue sensing/stimulation electrodes are checked for lower (voltage) thresholds at 910. In one example, the predetermined voltage threshold is 7.5 volts; however, the present leads, systems, and methods are not so limited. In another example, the predetermined voltage threshold may be set to a level determined by the physician. In yet another example, the predetermined voltage threshold may depend upon the lead type and the corresponding manufacturer's recommendation.

If the increased stimulation voltage is less than the predetermined voltage threshold, a determination of whether capture has been regain is made at 906. If capture is not regained, the process returns to 904 where the stimulation voltage is increased again. If capture is regained, at 907, the new stimulation voltage is evaluated. In one example, the evaluation 907 includes a balancing of input parameters (e.g., optimum pace location, voltage, voltage waveform shape, V-to-V or A-to-V pace delay, etc.) vs. output parameters (e.g., subject health, device longevity, voltage level which could potentially cause corrosion, etc.). If the evaluation is deemed acceptable, at 908, the new stimulation voltage is set. If the evaluation is deemed non-acceptable, the process returns to 904. At 909, the new stimulation voltage is retested/verified to ensure that it results in capture of the heart. If capture of the heart is not regained by the new stimulation voltage, the process returns to 904 where the stimulation voltage is increased again.

At 912, a determination of whether capture of the heart is regained by the new set of tissue sensing/stimulation electrodes is made. If capture of the heart is regained by the new set of tissue sensing/stimulation electrodes, at 913, the new stimulation vector is evaluated. In one example, the evaluation 913 includes a balancing of input parameters (e.g., optimum pace location, voltage, voltage waveform shape, V-to-V or A-to-V pace delay, etc.) vs. output parameters (e.g., subject health, device longevity, voltage level which could potentially cause corrosion, etc.). If the evaluation is deemed acceptable, at 914, the new stimulation vector is set. If the evaluation is deemed non-acceptable, the process returns to 910. At 915, the new stimulation voltage is retested/verified to ensure that it results in capture of the heart. If capture of the heart is not regained by the new set of tissue sensing/stimulation electrodes, a second new set of tissue sensing/stimulation electrodes are checked for lower (voltage) thresholds at 910.

Figure 10:
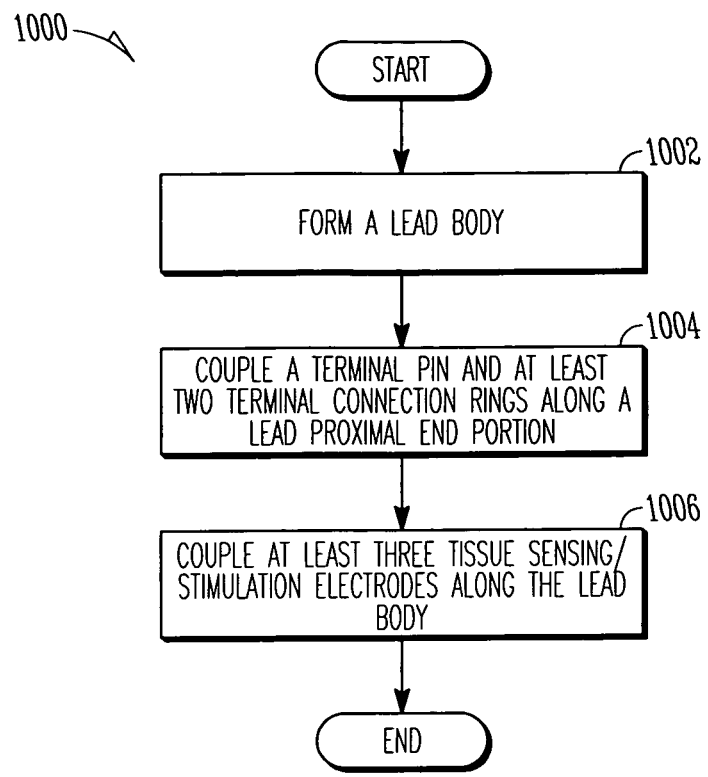
FIG. 10 is a flow chart illustrating a method of manufacturing a lead, as constructed in accordance with at least one embodiment.

FIG. 10 is a flow chart illustrating a method 1000 of manufacturing a lead for use in a system adapted to sense or stimulate a heart of a subject. At 1002, a lead body extending from one lead proximal end portion to one lead distal end portion is formed. In one example, forming the lead body includes forming a stylet or guidewire receiving cavity therein. In another example, forming the lead body includes forming at least one preformed biased portion adapted to return to a preformed shape upon removal of a stylet or a guidewire from the stylet or guidewire receiving cavity. In one such example, the preformed shape includes a two-dimensional shape, such as a curve or wave. In another such example, the preformed shape includes a three-dimensional shape, such as a spiral or other shape that conforms to heart anatomy such that the tissue sensing/stimulation electrodes are positioned as desired or to fixate the lead. The preformed biased portion is one option for increasing the probability of optimal or acceptable interfacing between tissue sensing/stimulation electrodes disposed on the lead and tissue or veins of the heart, such as a coronary vein. In yet another example, forming the lead body includes forming at least one arch in a vicinity of a tissue sensing/stimulation electrode, such as straddling the tissue sensing/stimulation electrode.

At 1004, a terminal pin and at least two terminal connection rings (collectively, one example of "terminal connections" referred to herein) are coupled along the one lead proximal end portion. In one example, the terminal pin and the at least two terminal connection rings are sized, shaped, and positioned to electrically and mechanically mate with electrical connections of a multi-pole connector cavity of a cardiac sensor/stimulator. At 1006, at least three tissue sensing/stimulation electrodes are coupled along the lead body. In varying examples, the method of manufacturing the lead further comprises disposing three or more conductors within the lead body, thereby electrically coupling the tissue sensing/stimulation electrodes and the terminal connections.

Figure 11:
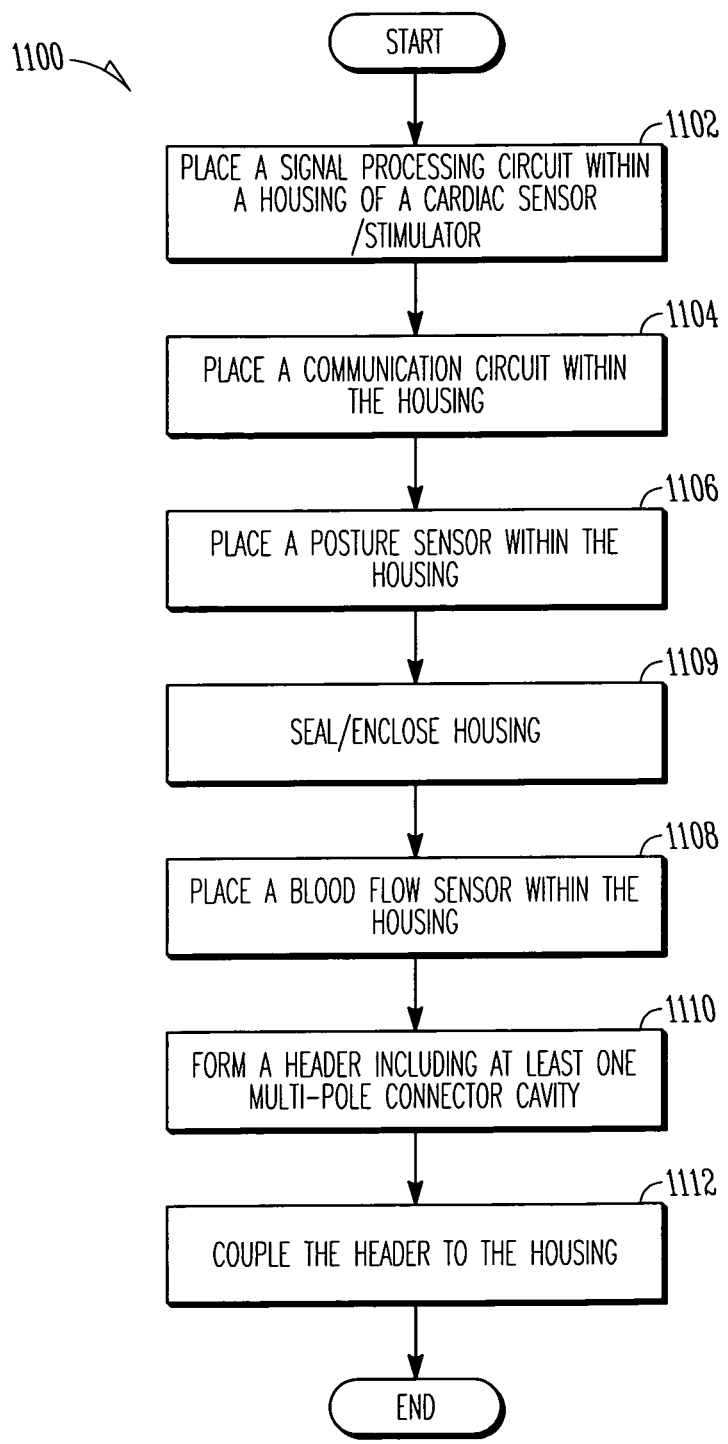
FIG. 11 is a flow chart illustrating a method of manufacturing a cardiac sensor/stimulator, as constructed in accordance with at least one embodiment.

FIG. 11 is a flow chart illustrating a method 1100 of manufacturing a cardiac sensor/stimulator for use in a system adapted to sense or stimulate a heart of a subject. At 1102, a signal processing circuit is placed within a housing of the cardiac sensor/stimulator. The signal processing circuit is adapted to sense or stimulate the heart of the subject by way of one or more (optimal or acceptable) tissue electrode configurations. In one example, the one or more tissue electrode configurations are selected using evaluations of one or a combination of a stimulation threshold parameter, a stimulation impedance parameter, a stimulation selection parameter, a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter. In one such example, the selection of the one or more tissue electrode configurations is manually communicated to the signal processing circuit (e.g., entered into an external-user interface by a user). In another such example, the selection of the one or more tissue electrode configuration is automatically performed by the signal processing circuit, such as a logic module. In yet another example, the selection of the one or more tissue electrode configuration is partly performed automatically and partly performed (i.e., made) by the user.

In addition to the signal processing circuit, many other circuits, modules, and other devices may also be included in the housing of the cardiac sensor/stimulator. At 1104, a communication circuit is placed within the housing of the cardiac sensor/stimulator. The communication circuit is adapted to receive one or more inputs from an external programmer. In one example, the one or more inputs include a selection of the optimal or acceptable tissue electrode configurations to be used to sense or stimulate the heart of the subject. At 1106, a posture sensor is placed within the housing of the cardiac sensor/stimulator; however, the posture sensor may instead be located remote from the cardiac sensor/stimulator. The posture sensor is adapted to sense a posture signal indicative of a subject's then-current posture. At 1108, a blood flow sensor circuit is placed within the housing of the cardiac sensor/stimulator; however, the blood flow sensor may instead be located remote from the cardiac sensor/stimulator. The blood flow sensor circuit is adapted to sense a blood flow signal indicative of a subject's then-current blood flow. At 1109, the housing is sealed/enclosed.

At 1110, a header including at least one multi-pole connector cavity disposed therein is formed. Each multi-pole connector cavity is sized and shaped to receive one lead proximal end portion having three or more terminal connections. At 1112, the header is coupled to the housing of the cardiac sensor/stimulator.

When functioning properly, a human heart maintains its own intrinsic rhythm, and is capable of pumping adequate blood throughout the body's circulatory system. However, some people have irregular cardiac rhythm, referred to as cardiac arrhythmias. Such arrhythmias result in diminished blood circulation. The leads, systems, and methods described herein provide an advantageous way of treating cardiac arrhythmias using stimulation therapy. As one example, through the use of a lead having a lead body extending from one lead proximal end portion to one lead distal end portion and including three or more tissue sensing/stimulation electrodes disposed therealong, the opportunity exists for a user (e.g., an implanting physician) or a cardiac sensor/stimulator itself to choose among numerous possible tissue electrode configurations for sensing or stimulating a subject's heart.

The numerous possible tissue electrode configurations allow the user or the cardiac sensor/stimulator to recurrently select one or more tissue electrode configurations which optimize one or a combination of a stimulation threshold parameter, a stimulation impedance parameter, a stimulation selection parameter (including reduction of phrenic nerve or diaphragmatic stimulation), a sense voltage parameter, a sense noise parameter, a tissue electrode location parameter, a heart chamber configuration parameter, a blood flow parameter, a posture parameter, a blood volume parameter, an acceleration or motion parameter, a spatial distance parameter, a time parameter, an impedance parameter, a blood oxygen parameter, or a stimulation energy parameter, all without having to physically move the lead after initial implantation.

Other advantages of the leads; systems, and methods described herein are as follows. As one example, the lead can accommodate unique, varying heart anatomies due to its three or more tissue sensing/stimulation electrodes disposed along the lead body. As another example, the system is adapted to accommodate changes in tissue electrode/heart tissue interface (i.e., improve probability of effective sensing heart tissue or stimulating excitable heart tissue) and changes in heart rhythm, which may occur over time. As yet another example, the lead reduces the need for multiple leads or lead legs to be implanted within the subject.

As mentioned above, this Detailed Description is not to be taken in a limiting sense, and the scope of various embodiments is defined only by the appended claims, along with the full range of legal equivalents to which such claims are entitled. In the appended claims, the term "including" is used as the plain-English equivalent of the term "comprising." Also in the following claims, the terms "including" and "comprising" are open-ended, that is, a system, device, article, or process that includes elements in addition to those listed after such a term in a claim are still deemed to fall within the scope of that claim.

What is claimed is:

1. A system, comprising:
   an implantable device configured to sense or receive cardiac signals and deliver cardiac stimulation; and
   a lead longitudinally extending from a single lead proximal end portion to a single lead distal end portion, the lead including
   a lead body, and
   four or more tissue electrodes disposed along the lead body, wherein at least two of the four or more tissue electrodes are configured for both sensing and stimulating and wherein all of the four or more electrodes are implantable within, on, or about a heart of a subject;
   the single lead proximal end portion of the lead is sized and shaped to couple to the implantable device, the coupling electrically connecting each of the four or more tissue electrodes to a signal processing circuit of the implantable device; and
   the signal processing circuit is adapted to sense in a first instance and stimulate in a second instance, the sensing and stimulation occurring by way of one or more selected tissue electrode configurations, wherein the basis of choosing a selected tissue electrode sensing configuration is an analysis of a plurality of different sensing configurations of the four or more tissue electrodes using one or more sense parameters, and wherein the signal processing circuit automatically selects one of the plurality of different sensing configurations of the four or more tissue electrodes for sensing after implantation in view of the analysis of the plurality of different sensing configurations of the four or more tissue electrodes, wherein the signal processing circuit is further adapted to select one of the plurality of different sensing configurations using, at least in part, one or a combination of a blood volume parameter, a spatial distance parameter, or a blood oxygen parameter, each parameter evaluated by way of a logic module.

2. The system as recited in claim 1, further comprising an external programmer including a telemetry device communicatively couplable to the signal processing circuit of the implantable device,
   the external programmer adapted to receive a user-derived selection of the one or more tissue electrode configurations and communicate the selection to the signal processing circuit.

3. The system as recited in claim 1, wherein the implantable device includes at least one multi-pole connector cavity, the at least one multi-pole connector cavity sized and shaped to receive and electrically engage with the single lead proximal end portion of the lead, which includes at least four terminal connections.

4. The system as recited in claim 1, wherein the one or more selected tissue electrode configurations include at least one tissue electrode positioned to sense or stimulate one or both of a left side of the heart or a right side of the heart.

5. The system as recited in claim 1, wherein the analysis of the plurality of different sensing and stimulating configurations of the four or more tissue electrodes includes evaluating the plurality of tissue electrode configurations for each configuration's ability to sense or stimulate the heart.

6. The system as recited in claim 1, wherein the implantable device includes one or a combination of a posture sensor, a blood flow sensor, a blood pressure sensor, an impedance sensor, a blood volume sensor, an acceleration or motion sensor, a spatial distance sensor, or a blood oxygen sensor.

7. The system as recited in claim 1, wherein the single lead proximal end portion of the lead includes at least four terminal connections.

8. The system as recited in claim 7, further comprising at least four conductors contained within the lead body of the lead, the at least four conductors extending between the at least four terminal connections and the four or more tissue electrodes.

9. The system as recited in claim 1, wherein the one or more selected tissue electrode configurations include an electrical coupling of at least two of the four or more tissue sensing electrodes.

10. The system as recited in claim 1, wherein the lead body of the lead includes a stylet or guidewire receiving cavity and at least one preformed biased portion, the preformed biased portion configured to return to a preformed shape upon removal of a stylet or guidewire from the stylet or guidewire receiving cavity.

11. The system as recited in claim 1, wherein the lead includes a first lead and a second lead, each of the first and second leads including at least four or more tissue electrodes.

12. The system as recited in claim 11, wherein the one or more selected tissue electrode configurations include a tissue electrode on the first lead and a tissue electrode on the second lead.

* * * * *